United States Patent
Ohashi

(10) Patent No.: US 9,230,058 B2
(45) Date of Patent: Jan. 5, 2016

(54) IMAGE PROCESSING DEVICE, IMAGE PROCESSING METHOD AND PROGRAM

(75) Inventor: Takeshi Ohashi, Tokyo (JP)

(73) Assignee: SONY CORPORATION, Tokyo (JP)

(*) Notice: Subject to any disclaimer, the term of this patent is extended or adjusted under 35 U.S.C. 154(b) by 237 days.

(21) Appl. No.: 13/349,970

(22) Filed: Jan. 13, 2012

(65) Prior Publication Data

US 2012/0188283 A1  Jul. 26, 2012

(30) Foreign Application Priority Data

Jan. 25, 2011  (JP) ................ P2011-012952

(51) Int. Cl.
| | | |
|---|---|---|
| G06F 19/00 | (2011.01) | |
| G06T 7/00 | (2006.01) | |
| G06F 17/30 | (2006.01) | |
| A61B 5/00 | (2006.01) | |

(52) U.S. Cl.
CPC ............ *G06F 19/321* (2013.01); *G06F 19/345* (2013.01); *G06T 7/0081* (2013.01); *A61B 5/7267* (2013.01); *A61B 2576/00* (2013.01); *G06F 17/30056* (2013.01); *G06T 2207/10056* (2013.01); *G06T 2207/30024* (2013.01)

(58) Field of Classification Search
None
See application file for complete search history.

(56) References Cited

U.S. PATENT DOCUMENTS

| | | | | |
|---|---|---|---|---|
| 7,660,488 B2* | 2/2010 | Reicher et al. | ................ | 382/299 |
| 7,852,356 B2* | 12/2010 | Takikawa et al. | ............. | 345/660 |
| 2006/0132507 A1* | 6/2006 | Wang | ............. | 345/660 |
| 2007/0041657 A1* | 2/2007 | Rychagov et al. | ............ | 382/274 |
| 2007/0297669 A1* | 12/2007 | Neal | ............. | 382/168 |
| 2008/0144941 A1* | 6/2008 | Togashi | ............. | 382/207 |
| 2010/0054611 A1* | 3/2010 | Nomura | ............. | 382/224 |
| 2010/0215279 A1* | 8/2010 | Gao et al. | ............. | 382/224 |
| 2011/0052060 A1* | 3/2011 | Furuya | ............. | 382/172 |

FOREIGN PATENT DOCUMENTS

| | | |
|---|---|---|
| JP | 2005-266718 | 9/2005 |
| JP | 2006-228185 | 8/2006 |

* cited by examiner

*Primary Examiner* — Jeffery A Brier
*Assistant Examiner* — Steven Elbinger
(74) *Attorney, Agent, or Firm* — Hazuki International, LLC

(57) ABSTRACT

An image processing device includes: a first feature amount extraction unit configured to extract a first feature amount from an image; a position detection unit configured to detect observation positions from the image based on a position detection dictionary, and the first feature amount extracted from the image; a second feature amount extraction unit configured to extract a second feature amount from the observation position; an observation-order determining unit configured to determine the order of observing the observation positions based on an order generation dictionary, and respective second feature amounts of the observation positions; and an image generation unit configured to generate observation images for displaying the observation positions in the observation order based on the image, the detected observation positions and the determined observation order.

9 Claims, 15 Drawing Sheets

IMAGE PROCESSING DEVICE, IMAGE PROCESSING METHOD AND PROGRAM

FIELD

The present disclosure relates to an image processing device, an image processing method and a program, and particularly relates to an image processing device, an image processing method and a program thereof capable of obtaining pathological images for diagnosis more simply and swiftly.

BACKGROUND

There are cases where a doctor or the like observes pathological images obtained by using a microscope and so on to make a pathological diagnosis, and techniques useful in making a diagnosis by using pathological images have been proposed.

As one of techniques, there is proposed a technique of generating a screening (moving observation) moving image, a zooming moving image and a focusing moving image using microscopic images taken by the microscope in accordance with, for example, an operation input by a user (for example, see JP-A-2006-228185 (Patent Document 1)). In the technique, the moving image can be generated in accordance with histories of operation inputs in the past and the operation input at present.

Additionally, there is also provided a technique of generating images for teaching materials of pathological diagnostics by imaging observed regions of a sample with resolution necessary for observation, associating the images obtained by the imaging with each other and recording them based on an observation log by an advising doctor (for example, see JP-A-2005-266718 (Patent Document 2)).

SUMMARY

Though the pathological diagnosis can be made more effectively by generating pathological images for diagnosis in the above techniques, complicated operations are necessary for obtaining such pathological images.

For example, it is necessary that the user perform an operation input for obtaining the screening moving image and so on as pathological images for diagnosis in the technique described in Patent Document 1. It is necessary that the user performs many operation inputs manually particularly with respect to a new microscopic image, therefore, it takes time to obtain the screening moving image and so on.

In view of the above, it is desirable to obtain pathologic images for diagnosis more simply and swiftly.

An embodiment of the present disclosure is directed to an image processing device including a first feature amount extraction unit configured to extract a first feature amount from an image to be processed, a position detection unit configured to detect observation positions from the image based on a position detection dictionary for detecting observation positions as positions to which attention should be given on the image from the first feature amount, which has been generated by statistical learning in advance, and the first feature amount extracted from the image, a second feature amount extraction unit configured to extract a second feature amount from the observation position on the image, an observation-order determining unit configured to determine the order of observing the observation positions on the image based on an order generation dictionary for determining the order in which respective observation positions on the image should be observed from the second feature amount, which has been generated by statistical learning in advance, and respective second feature amounts of the observation positions on the image and an image generation unit configured to generate observation images for displaying the observation positions on the image in the observation order based on the image, the detected observation positions and the determined observation order.

In the image processing device, the image may be a medical image.

The image processing device may further include a third feature amount extraction unit configured to extract a third feature amount from the observation position on the image and an observation-condition determining unit for determining an observation condition in each observation position on the image based on an observation-condition generation dictionary for determining the observation conditions of the observation positions on the image from the third feature amount, which has been generated by statistical learning in advance, and the third feature amount of the observation position on the image, in which the image generation unit can generate the observation images so that the observation position is displayed with the determined observation condition.

The observation condition may be display magnification of the observation position or display time during which the observation position is continuously displayed.

The observation images may be a moving image in which the observation positions are sequentially displayed in the observation order, and the whole image is displayed at least at the first or at the last of the moving image.

The observation images may be a moving image in which the observation positions are sequentially displayed in the observation order, and the whole image is displayed after one observation position is displayed, then, the next observation position is displayed in the moving image.

The observation images may be a moving image in which the observation positions are sequentially displayed in the observation order in a state in which the whole image is continuously displayed in a partial region in the observation images.

Another embodiment of the present disclosure is directed to an image processing method or an image processing program includes extracting a first feature amount from an image to be processed, detecting observation positions from the image based on a position detection dictionary for detecting observation positions as positions to which attention should be given on the image from the first feature amount, which has been generated by statistical learning in advance, and the first feature amount extracted from the image, extracting a second feature amount from the observation position on the image, determining the order of observing the observation positions on the image based on an order generation dictionary for determining the order in which respective observation positions on the image should be observed from the second feature amount, which has been generated by statistical learning in advance, and respective second feature amounts of the observation positions on the image, and generating observation images for displaying the observation positions on the image in the observation order based on the image, the detected observation positions and the determined observation order.

According to the embodiments of the present disclosure, a first feature amount is extracted from an image to be processed, observation positions are detected from the image based on a position detection dictionary for detecting observation positions as positions to which attention should be given on the image from the first feature amount, which has been generated by statistical learning in advance, and the first feature amount extracted from the image, a second feature amount is extracted from the observation position on the image, the order of observing the observation positions on the image is determined based on an order generation dictionary for determining the order in which respective observation positions on the image should be observed from the second feature amount, which has been generated by statistical learning in advance, and respective second feature amounts of the observation positions on the image, and observation images for displaying the observation positions on the image in the observation order based on the image, the detected observation positions and the determined observation order are generated.

According to the embodiments of the present disclosure, pathological images for diagnosis can be obtained more simply and swiftly.

DETAILED DESCRIPTION

Hereinafter, an embodiment to which the present disclosure is applied will be explained with reference to the drawings.
<First Embodiment>
[Configuration Example of Image Processing Device]

Figure 1:
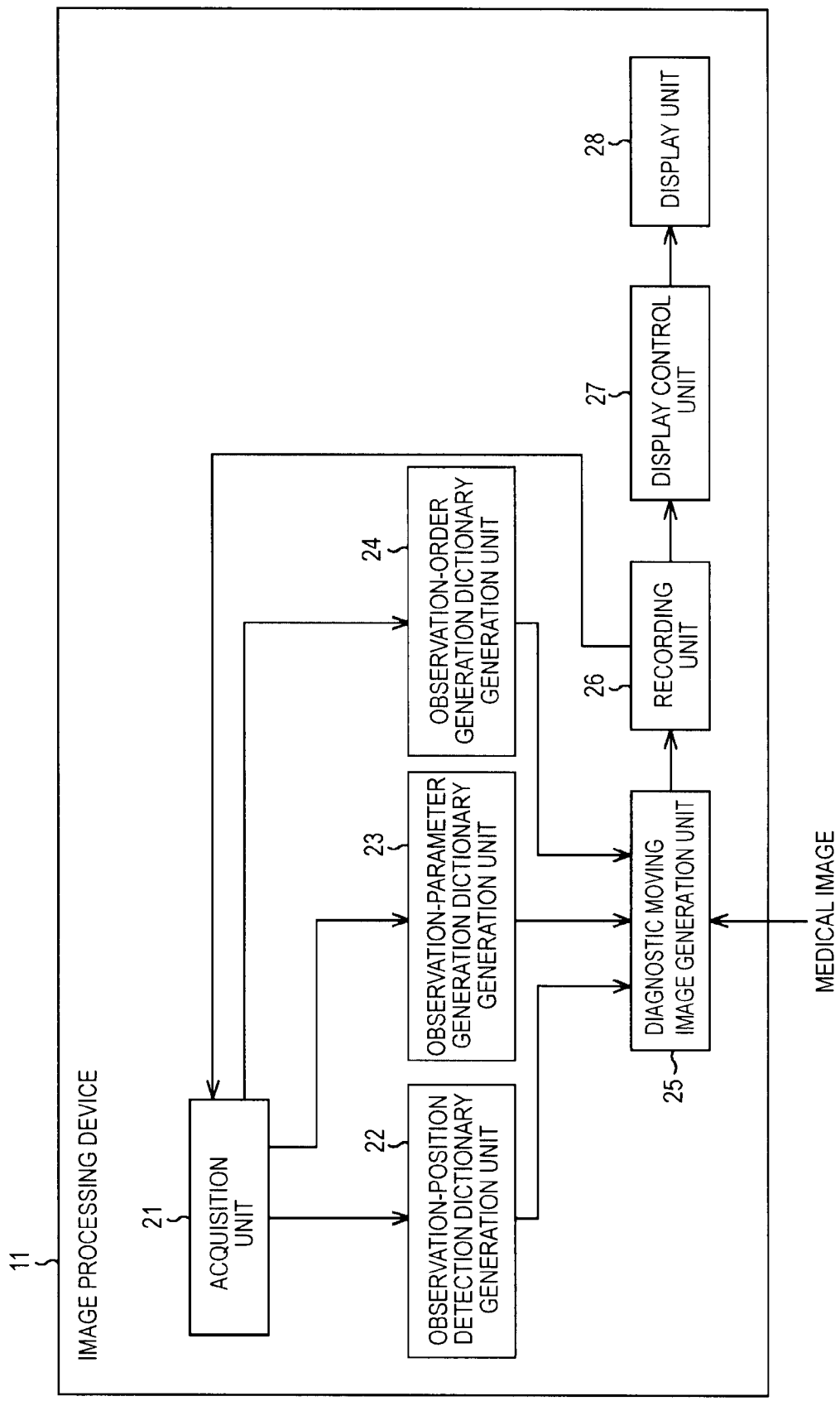
FIG. 1 is a diagram showing a configuration example of an image processing device according to an embodiment.

FIG. 1 is a diagram showing a configuration example of an embodiment of an image processing device to which the present disclosure is applied. An image processing device 11 generates a diagnostic moving image used for pathological diagnosis by a doctor or the like based on a medical image taken by, for example, a microscope and reproduces the moving image.

Any medical image can be used as long as it is a common medical image, and an example in which the medical image is an image for pathological diagnosis will be explained. The medical image is not limited to two-dimensional image data but can be three-dimensional image data such as CT (Computed Tomography) and MRI (Magnetic Resonance Image).

The image processing device 11 includes an acquisition unit 21, an observation-position detection dictionary generation unit 22, an observation-parameter generation dictionary generation unit 23, an observation-order generation dictionary generation unit 24, a diagnostic moving image generation unit 25, a recording unit 26, a display control unit 27 and a display unit 28.

The acquisition unit 21 acquires and records a medical image for learning and an observation log to be used for learning processing performed in the observation-position detection dictionary generation unit 22, the observation-parameter generation dictionary generation unit 23 and the observation-order generation dictionary generation unit 24. For example, medical images for learning are acquired from the recording unit 26. The acquisition unit 21 supplies the medical image for learning and the observation log to the observation-position detection dictionary generation unit 22, the observation-parameter generation dictionary generation unit 23 and observation-order generation dictionary generation unit 24 if necessary.

Here, the observation log is a log of observation obtained by observing respective regions of the medical image for learning displayed by using a pathological image viewer by a skillful doctor or the like while changing display magnification and the like. In more detail, the acquisition unit 21 acquires a log of observation at every second at the time of displaying the medical image for learning and processes the log obtained as the result of acquisition as an observation log.

The observation-position detection dictionary generation unit 22 performs statistical learning by using medical images for learning and the observation logs supplied from the acquisition unit 21 to generate an observation-position detection dictionary for detecting positions of regions which should be observed with attention on an arbitrary medical image for pathological diagnosis from the medical image.

For example, regions which should be observed with attention on the medical image are regions necessary for diagnosis of a tumor and so on, namely, target regions which should be examined by the doctor. Hereinafter, positions of regions to be observed with attention which are detected by the observation-position detection dictionary and positions of regions observed by the skillful doctor or the like with attention in the medical images for learning are referred to also as observation positions.

The observation-parameter generation dictionary generation unit 23 performs statistical learning by using medical images for learning and observation logs supplied from the acquisition unit 21 to generate an observation-parameter generation dictionary for determining various parameters to be set at the time of observing respective observation positions on the medical image for pathological diagnosis.

For example, various parameters at the time of observing respective observation positions are defined as observation conditions such as display magnification and observation time (display time) of observation positions. Hereinafter, parameters indicating these observation conditions obtained by using the observation-parameter generation dictionary are referred to as observation parameters.

The observation-order generation dictionary generation unit 24 performs statistical learning by using medical images for learning and observation logs supplied from the acquisition unit 21 to generate an observation-order generation dictionary for determining the order in which respective observation positions on the medical image for pathological diagnosis should be observed.

The diagnostic moving image generation unit 25 acquires and holds respective dictionaries generated in the observation-position detection dictionary generation unit 22, the observation-parameter generation dictionary generation unit 23 and the observation-order generation dictionary generation unit 24 as well as generates a diagnostic moving image from the inputted medical image by using these dictionaries to be supplied to the recording unit 26.

The recording unit 26 records the diagnostic moving image supplied from the diagnostic moving image generation unit 25 as well as supplies the diagnostic moving image to the display control unit 27 and the acquisition unit 21. The display control unit 27 supplies the diagnostic moving image supplied from the recording unit 26 to the display unit 28 and controls reproduction of the diagnostic moving image. The display unit 28 includes, for example, a liquid crystal display and so on, displaying a diagnostic moving image under control by the display control unit 27.

[Configuration Example of Observation-Position Detection Dictionary Generation Unit]

Next, more detailed configuration examples of the observation-position detection dictionary generation unit 22, the observation-parameter generation dictionary generation unit 23 and the observation-order generation dictionary generation unit 24 as well as the diagnostic moving image generation unit 25 in FIG. 1 will be explained.

Figure 2:
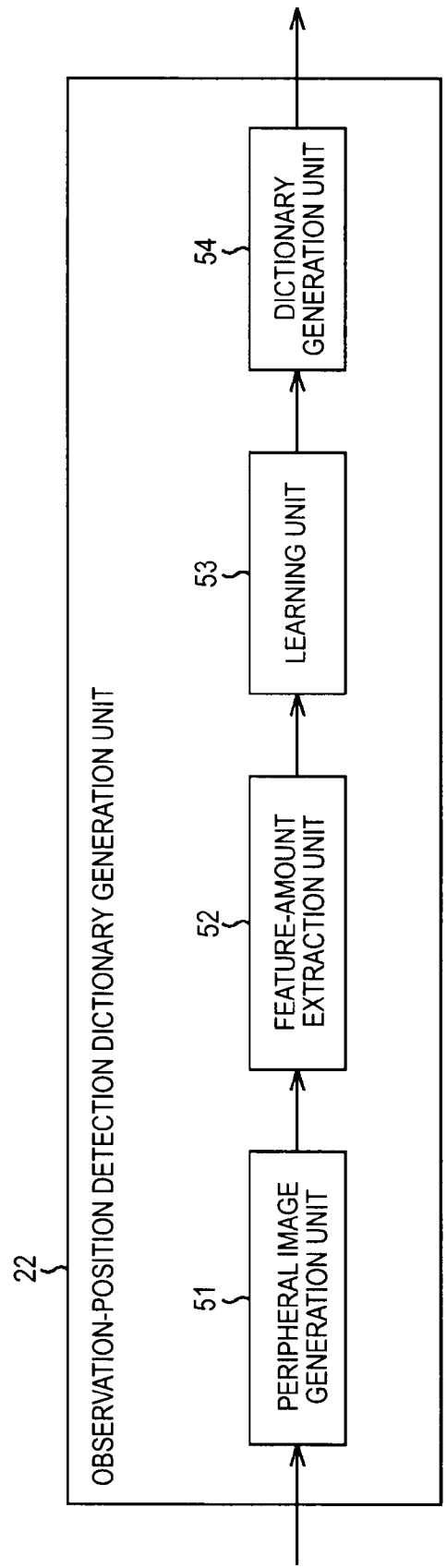
FIG. 2 is a diagram showing a configuration example of an observation-position detection dictionary generation unit.

FIG. 2 is a diagram showing a configuration example of the observation-position detection dictionary generation unit 22.

The observation-position detection dictionary generation unit 22 includes a peripheral image generation unit 51, a feature amount extraction unit 52, a learning unit 53 and a dictionary generation unit 54.

The peripheral image generation unit 51 acquires a medical image for learning and an observation log from the acquisition unit 21 and cuts out partial regions of the medical image for learning as peripheral images to be supplied to the feature amount extraction unit 52. At this time, cutout of peripheral images is performed based on the observation log.

The feature amount extraction unit 52 extracts feature amounts of a predetermined feature from plural peripheral images supplied from the peripheral image generation unit 51 and supplies the feature amounts to the learning unit 53. The learning unit 53 performs statistical learning based on the feature amounts supplied from the feature amount extraction unit 52 and supplies the learning result to the dictionary generation unit 54. The dictionary generation unit 54 generates the observation-position detection dictionary based on the learning result from the learning unit 53 and supplies the dictionary to the diagnostic moving image generation unit 25.

[Configuration Example of Observation-Parameter Generation Dictionary Generation Unit]

Figure 3:
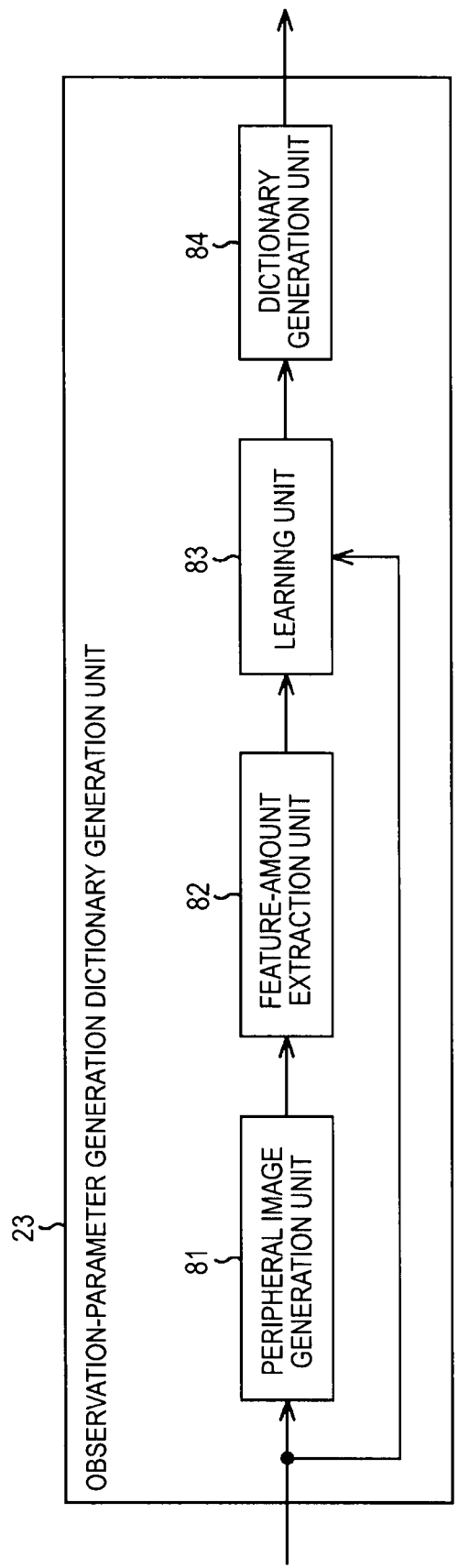
FIG. 3 is a diagram showing a configuration example of an observation-parameter generation dictionary generation unit.

FIG. 3 is a diagram showing a configuration example of the observation-parameter generation dictionary generation unit 23. The observation-parameter generation dictionary generation unit 23 includes a peripheral image generation unit 81, a feature amount extraction unit 82, a learning unit 83 and a dictionary generation unit 84.

These units from peripheral image generation unit 81 to the dictionary generation unit 84 are basically the same as the units from the peripheral image generation unit 51 to the dictionary generation unit 54 of FIG. 2 except that algorithm for learning and the feature amount to be extracted differ, therefore, the explanation thereof is omitted.

However, the statistical learning is performed in the learning unit 83 by using the feature amounts extracted from the peripheral images and observation logs supplied from the acquisition unit 21. The observation-parameter generation dictionary generated in the dictionary generation unit 84 is supplied to the diagnostic moving image generation unit 25.

[Configuration Example of Observation-Order Generation Dictionary Generation Unit]

Figure 4:
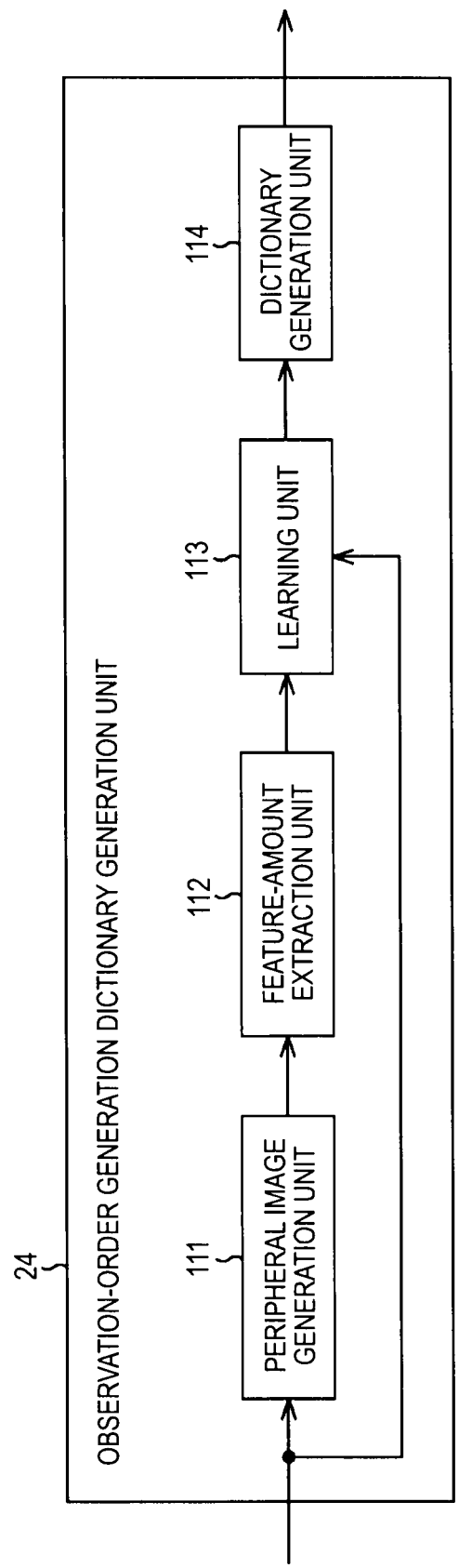
FIG. 4 is a diagram showing a configuration example of an observation-order generation dictionary generation unit.

FIG. 4 is a diagram showing a configuration example of the observation-order generation dictionary generation unit 24. The observation-order generation dictionary generation unit 24 includes a peripheral image generation unit 111, a feature amount extraction unit 112, a learning unit 113 and a dictionary generation unit 114.

These units from peripheral image generation unit 111 to the dictionary generation unit 114 are basically the same as the units from the peripheral image generation unit 51 to the dictionary generation unit 54 of FIG. 2 except that algorithm for learning and the feature amount to be extracted differ, therefore, the explanation thereof is omitted.

However, the statistical learning is performed in the learning unit 113 by using the feature amounts extracted from the peripheral images and observation logs supplied from the acquisition unit 21. The observation-order generation dictionary generated in the dictionary generation unit 114 is supplied to the diagnostic moving image generation unit 25.

The peripheral images generated in the peripheral image generation unit 51, the peripheral image generation unit 81 and the peripheral image generation unit 111 may be the same size as well as different sizes.

[Configuration Example of Diagnostic Moving Image Generation Unit]

Figure 5:
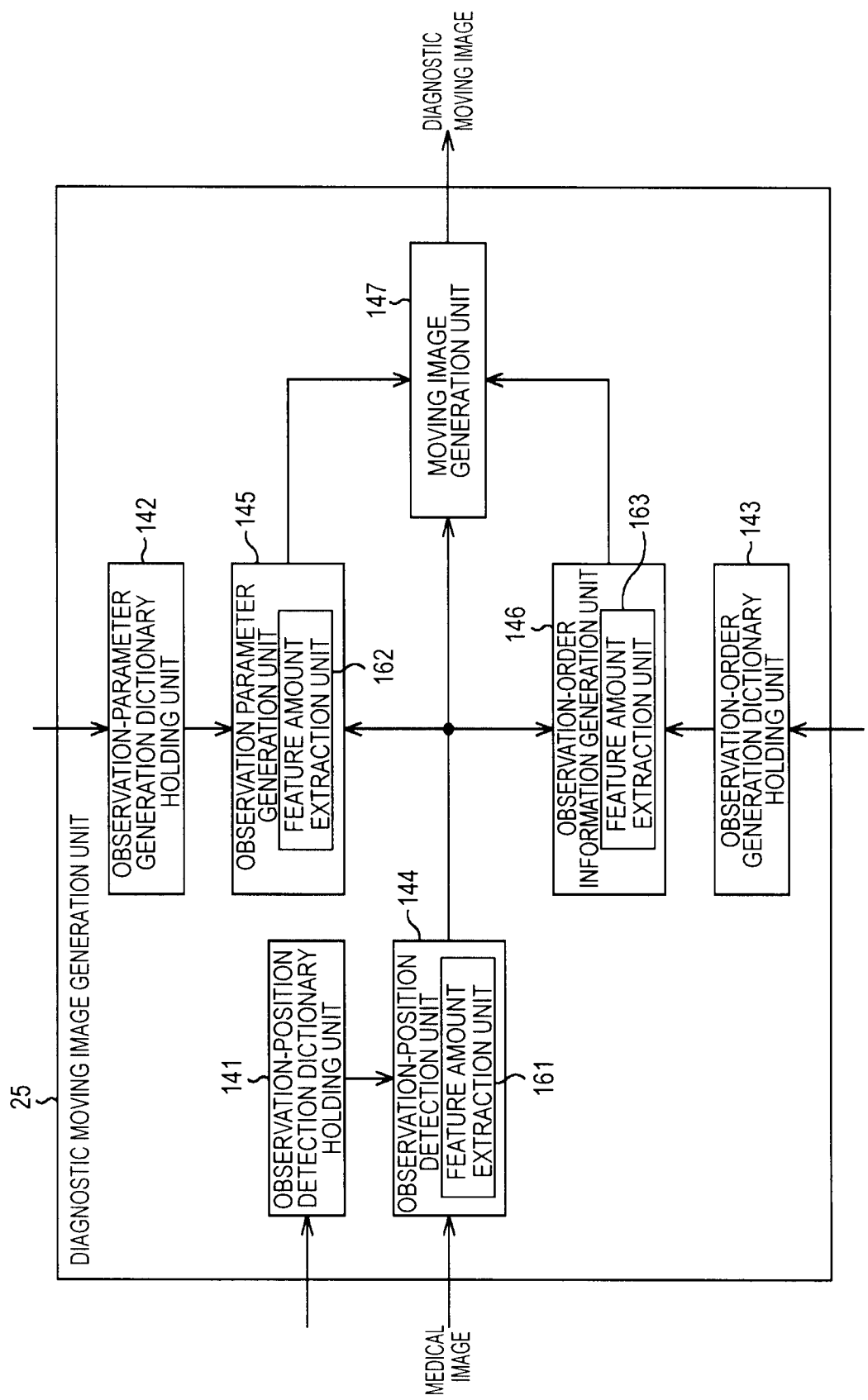
FIG. 5 is a diagram showing a configuration example of a diagnostic moving image generation unit.

Moreover, FIG. 5 is a diagram showing a configuration example of the diagnostic moving image generation unit 25.

The diagnostic moving image generation unit 25 includes an observation-position detection dictionary holding unit 141, an observation-parameter generation dictionary holding unit 142, an observation-order generation dictionary holding unit 143, an observation-position detection unit 144, an observation-parameter generation unit 145, an observation-order information generation unit 146 and a moving image generation unit 147.

The observation-position detection dictionary holding unit 141, the observation-parameter generation dictionary holding unit 142 and the observation-order generation dictionary holding unit 143 hold the observation-position detection dictionary, the observation-parameter generation dictionary and the observation-order generation dictionary supplied from the observation-position detection dictionary generation unit 22, the observation-parameter generation dictionary generation unit 23 and the observation-order generation dictionary generation unit 24.

The observation-position detection unit 144 detects observation positions from the supplied medical image by using the observation-position detection dictionary recorded in the observation-position detection dictionary holding unit 141 and supplies the detected result and the medical image to the observation-parameter generation unit 145, the observation-order information generation unit 146 and the moving image generation unit 147. The observation-position detection unit 144 includes a feature amount extraction unit 161, which extracts feature amounts used for detection of observation positions from the medical image at the time of detecting the observation positions.

The observation-parameter generation unit 145 generates observation parameters at respective observation positions on the medical image based on the detected result and the medical image supplied from the observation-position detection unit 144 and the observation-parameter generation dictionary stored in the observation-parameter generation dictionary holding unit 142, supplying the observation parameters to the moving image generation unit 147.

The observation-parameter generation unit 145 includes a feature amount extraction unit 162, which extracts feature amounts used for generation of observation parameters from the medical image supplied from the observation-position detection unit 144 at the time of generating observation parameters.

The observation-order information generation unit 146 generates observation order information indicating the observation order of observation positions on the medical image based on the detected result and medical image supplied from the observation-position detection unit 144 as well as the observation order generation dictionary held in the observation-order generation dictionary holding unit 143, supplying the information to the moving image generation unit 147.

The observation-order information generation unit 146 includes a feature amount extraction unit 163, which extracts feature amounts used for generation of observation order information from the medical image supplied from the observation position detection unit 144 at the time of generating observation order information.

The moving image generation unit 147 generates a diagnostic moving image based on the detected result of observation positions and medical image from the observation-position detection unit 144, observation parameters from the observation-parameter generation unit 145 and observation order information from the observation-order information generation unit 146, supplying the diagnostic moving image to the recording unit 26.

[Concerning Generation of Observation Log]

When the skillful doctor or the like operates the image processing device 11 and instructs the device to display the medical image for learning as the pathological image for pathological diagnosis, the display control unit 27 acquires the medical image for learning from the recording unit 26 and supplies the image to the display unit 28 to be displayed thereon. At this time, the display control unit 27 displays partial regions of the medical image for learning by zooming in the regions or performs scroll display from a given region to another region in accordance with operation by the skillful doctor or the like.

Figure 6:
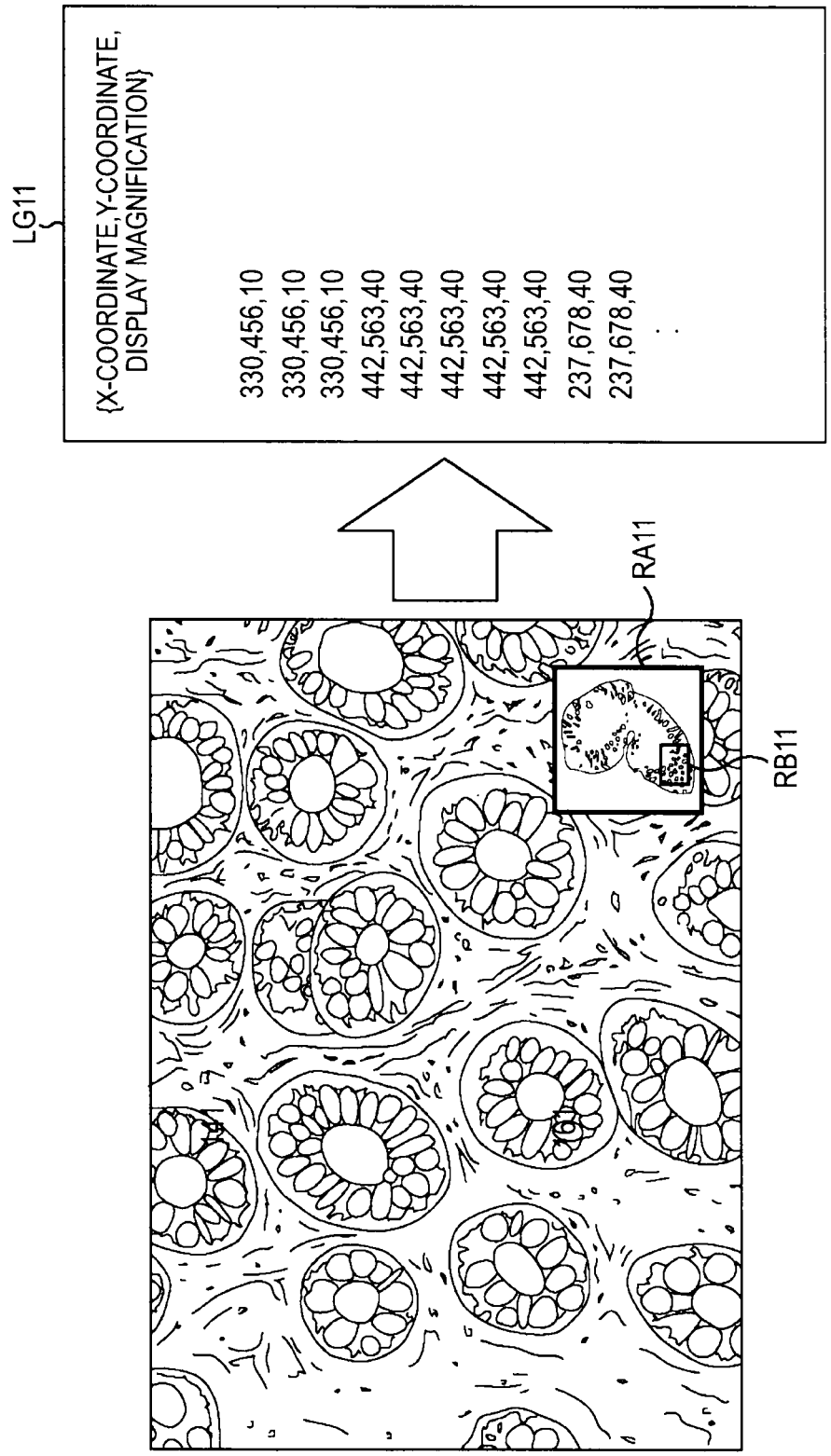
FIG. 6 is a view for explaining generation of an observation log.

According to the above, the medical image for learning, for example, shown on the left side of FIG. 6 is displayed on the display unit 28. In the example of FIG. 6, the whole medical image for learning to be displayed is displayed in a region RA11 provided on the lower right in the drawing of the display screen of the display unit 28, and a partial region of the medical image for learning is displayed on the whole display screen of the display unit 28. That is, an image of a region RB11 on the medical image for learning in the region RA11 is zoomed in and displayed in the whole display screen of the display unit 28.

The skillful doctor or the like makes a pathological diagnosis by observing respective regions of the medical image for learning displayed on the display unit 28. For example, the skillful doctor or the like finds out a cancer or determines the progress degree of the cancer.

When the skillful doctor or the like observes respective regions of the medical image for learning by zooming in/zooming out these regions with a given display magnification, the acquisition unit 21 acquires the displayed medical image for learning from the recording unit 26 as well as records a log of observation of the medical image for learning at every second.

Accordingly, a log LG11 at respective seconds, for example, shown on the right side of FIG. 6 can be obtained. In the log LG11, data including observation positions by the skillful doctor at respective time points and the display magnification is vertically aligned in the order of time.

Here, the observation position is the central position of the region displayed on the display unit 28 on the medical image for learning, which is represented by an X-coordinate and a Y-coordinate in the XY coordinate system with a given position on the medical image for learning as an origin. The display magnification is a display magnification (zooming magnification) at the time of displaying the observation position of the medical image for learning.

In the example of FIG. 6, data including {X-coordinate, Y-coordinate, display magnification} is vertically aligned in the drawing as data of the log at respective time points. Therefore, for example, it is found that the skillful doctor or the like has observed the position on the medical image for learning fixed by an X-coordinate "330" and a Y-coordinate "456" by zooming the image with the display magnification of 10 times.

When the observation of the medical image for learning by the skillful doctor or the like is completed, the acquisition unit 21 generates an observation log from the log obtained at every second to be recorded as the observation log for learning.

Figure 7:
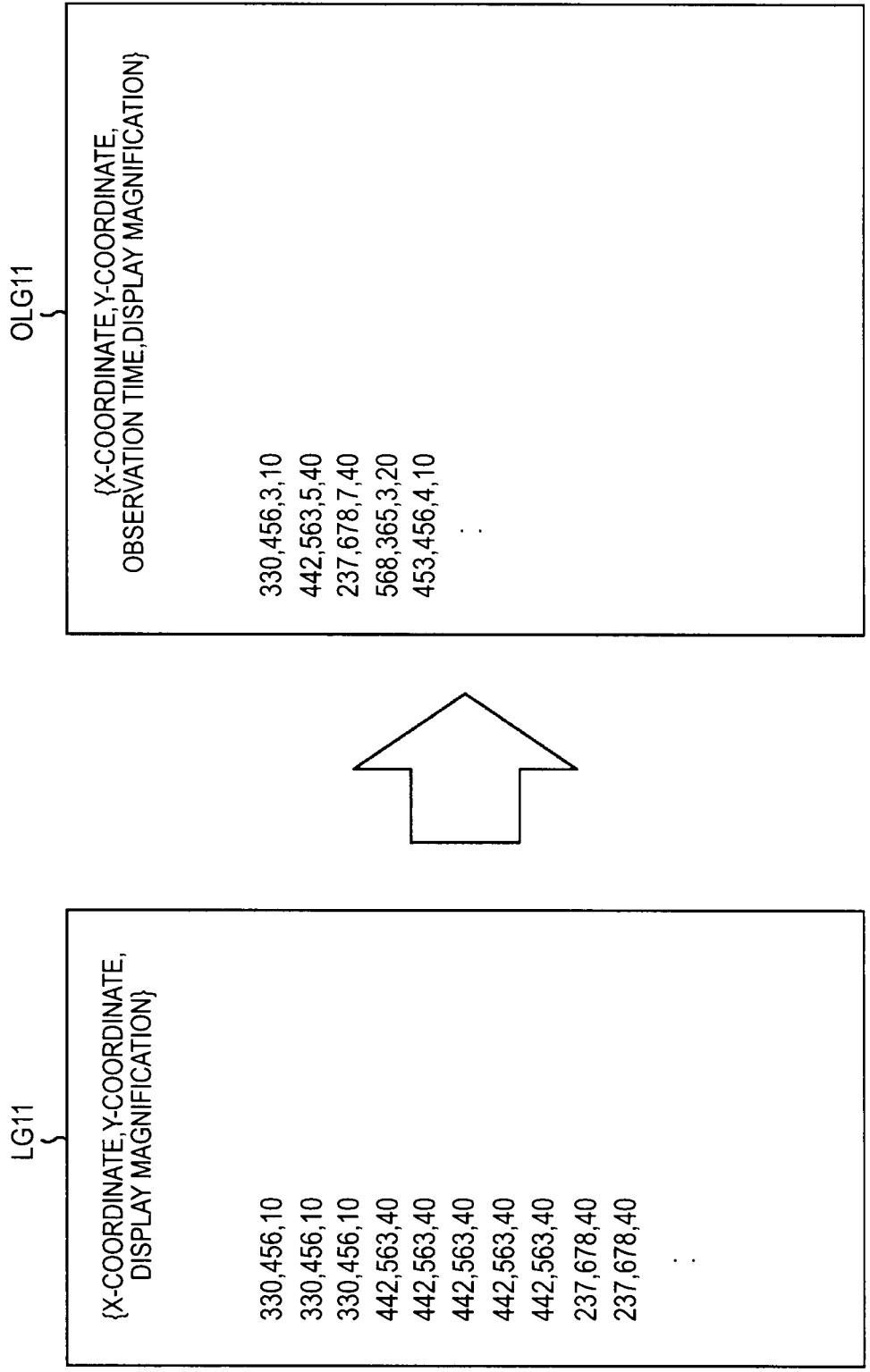
FIG. 7 is a diagram for explaining generation of the observation log.

For example, the acquisition unit 21 generates an observation log OLG11 including X-coordinates, Y-coordinates observation time and display magnifications of respective observation positions of the medical image for learning from the log LG11 obtained at every second including the X-coordinates, the Y-coordinates and the display magnifications at respective time points as shown in FIG. 7.

In the observation log OLG11, data including {X-coordinate, Y-coordinate, observation time, display magnification} at respective observation positions on the medical image for learning which has been observed by the skillful doctor or the like is vertically aligned in the drawing in the order of time as data of the log.

For example, top three data in the log LG11 of FIG. 7 is {330, 456, 10}, which is the same data. Therefore, it is found that the skillful doctor or the like has observed the region on the medical image for learning fixed by the X-coordinate "330" and the Y-coordinate "456" for three seconds with the display magnification of 10 times.

Accordingly, the acquisition unit 21 generates data {330, 456, 3, 10} shown at the top of the observation log OLG11 in the drawing from these data. Here, an observation time "3" indicates that the region on the medical image for learning determined by the data has been continuously observed for three seconds. That is, the observation time indicates a period of time during which the region on the medical image for learning has been continuously displayed.

After the observation log is generated as the above, the acquisition unit 21 records the acquired medical image for learning and the observation log by associating them with each other.

When generating the observation log, it is also preferable that a log obtained when the skillful doctor or the like has not actually make a pathological diagnosis is not reflected on the generation of the observation log.

For example, assume that the skillful doctor or the like breaks off the diagnosis due to some factors when making a pathological diagnosis using the medical image for learning. In this case, the log is recorded during time from the breaking off of diagnosis until restart of diagnosis though the diagnosis has not been actually made by the skillful doctor or the like, as a result, the observation time in the observation position displayed during the period will be long more than necessary.

Accordingly, for example, a sensor for detecting the direction of a sight line of the skillful doctor or the like performing operation of the image processing device 11 is provided in the image processing device 11, thereby detecting whether the skillful doctor or the like actually makes a pathological diagnosis or not. For example, when the sight line of the skillful doctor or the like apparently deviates from the direction of the display unit 28, it is determined that the pathological diagnosis is not made.

When it is determined that the pathological diagnosis is not made as the above, the acquisition unit 21 restrains recording of the log of the medical image for learning at every second until the direction of the sight line of the skillful doctor or the like is detected to be the direction of the display unit 28. Accordingly, a more accurate observation log can be obtained.

[Explanation of Learning Processing of Observation-Position Detection Dictionary]

When the sufficient number of medical images for learning and observation logs are obtained by the acquisition unit 21, the observation-position detection dictionary generation unit 22, the observation-parameter generation dictionary generation unit 23 and the observation-order generation dictionary generation unit 24 perform leaning by using these medical images for learning and observation logs to generate respective dictionaries.

Hereinafter, generation of these dictionaries will be explained.

First, leaning processing of the observation-position detection dictionary by the observation-position detection dictionary generation unit 22 will be explained with reference to a flowchart of FIG. 8.

In Step S11, the peripheral image generation unit 51 cuts out peripheral images of observation positions and non-observation positions on the medical image for learning based on the medical image for learning and the observation log supplied from the acquisition unit 21 and supplies the images to the feature amount extraction unit 52.

Figure 9:
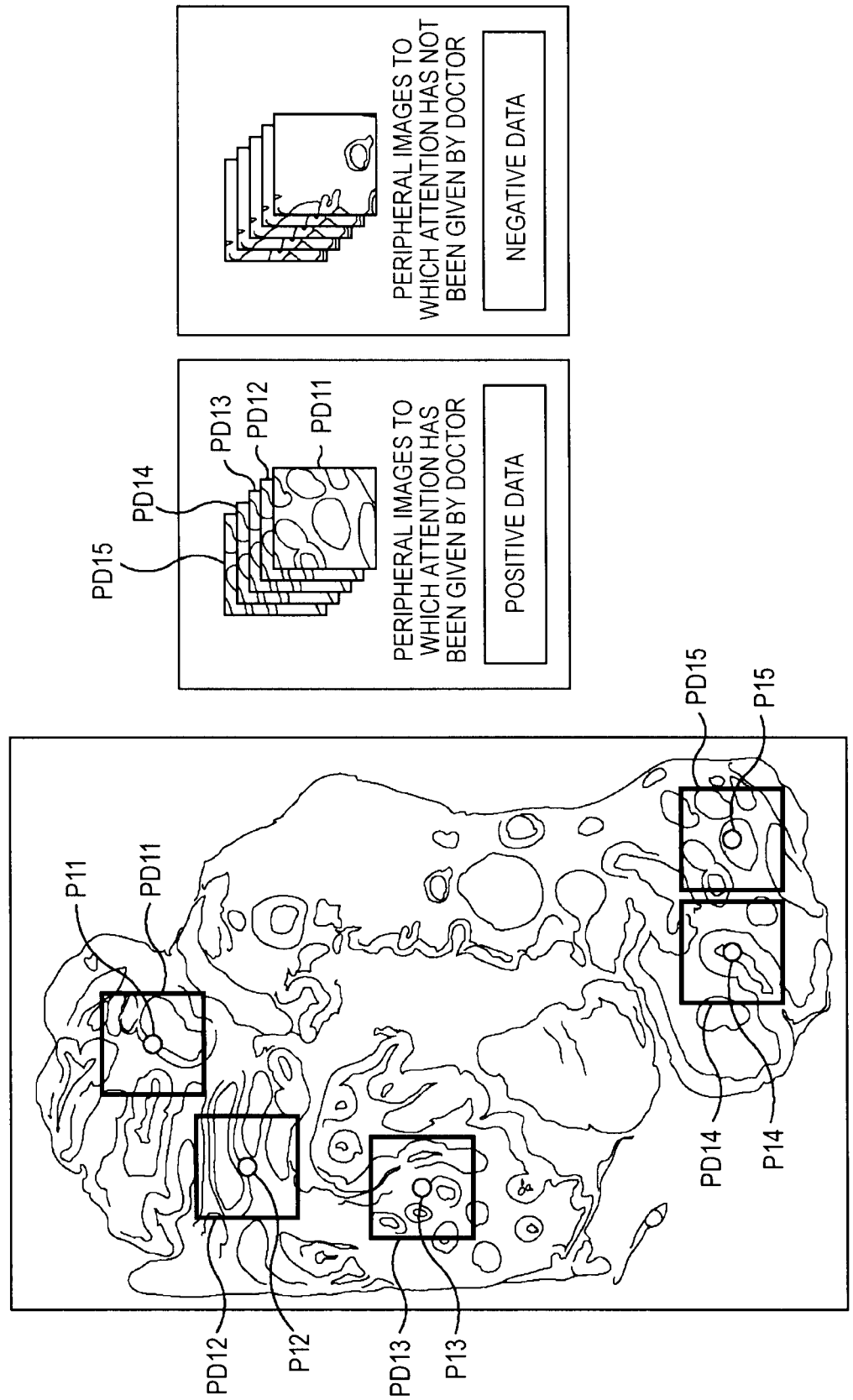
FIG. 9 is a view for explaining the learning of the observation-position detection dictionary.

For example, assume that the medical image for learning shown in FIG. 9 is supplied and five observation positions P11 to P15 are determined by the observation log. In this case, the peripheral image generation unit 51 cuts out respective rectangular regions including these observation positions P11 to P15 at centers of these regions to be peripheral images PD11 to PD15 including the observation positions.

The peripheral image generation unit 51 also determines some positions different from the observation positions on the medical image for learning as non-observation positions and cuts out respective rectangular regions including these non-observation positions at the centers of these regions to be peripheral images of the non-observation positions. The non-observation positions are fixed at random by the peripheral image generation unit 51.

The peripheral images PD11 to PD15 of the observation positions obtained as the above are images of regions to which attention has been given by the skillful doctor or the like at the pathological diagnosis. That is, theses are regions which have been continuously displayed for more than a fixed period of time at the time of pathological diagnosis. On the other hand, the peripheral images of non-observation positions are images of regions to which attention has not been particularly given by the skillful doctor or the like.

The peripheral image generation unit 51 supplies the peripheral images PD11 to PD15 to the feature amount extraction unit 52 as positive data and supplies the peripheral images of the non-observation positions to the feature amount extraction unit 52 as negative data as shown on the right side of the drawing. For example, discrimination between positive data and negative data is made by adding labels indicating which of these data to the peripheral images.

The size of the region cut out from the medial image for learning as the peripheral image may be the predetermined size, or it is also preferable that statistical learning of the observation-position detection dictionary is performed while changing the size and the optimum size will be fixed on the process.

Figure 8:
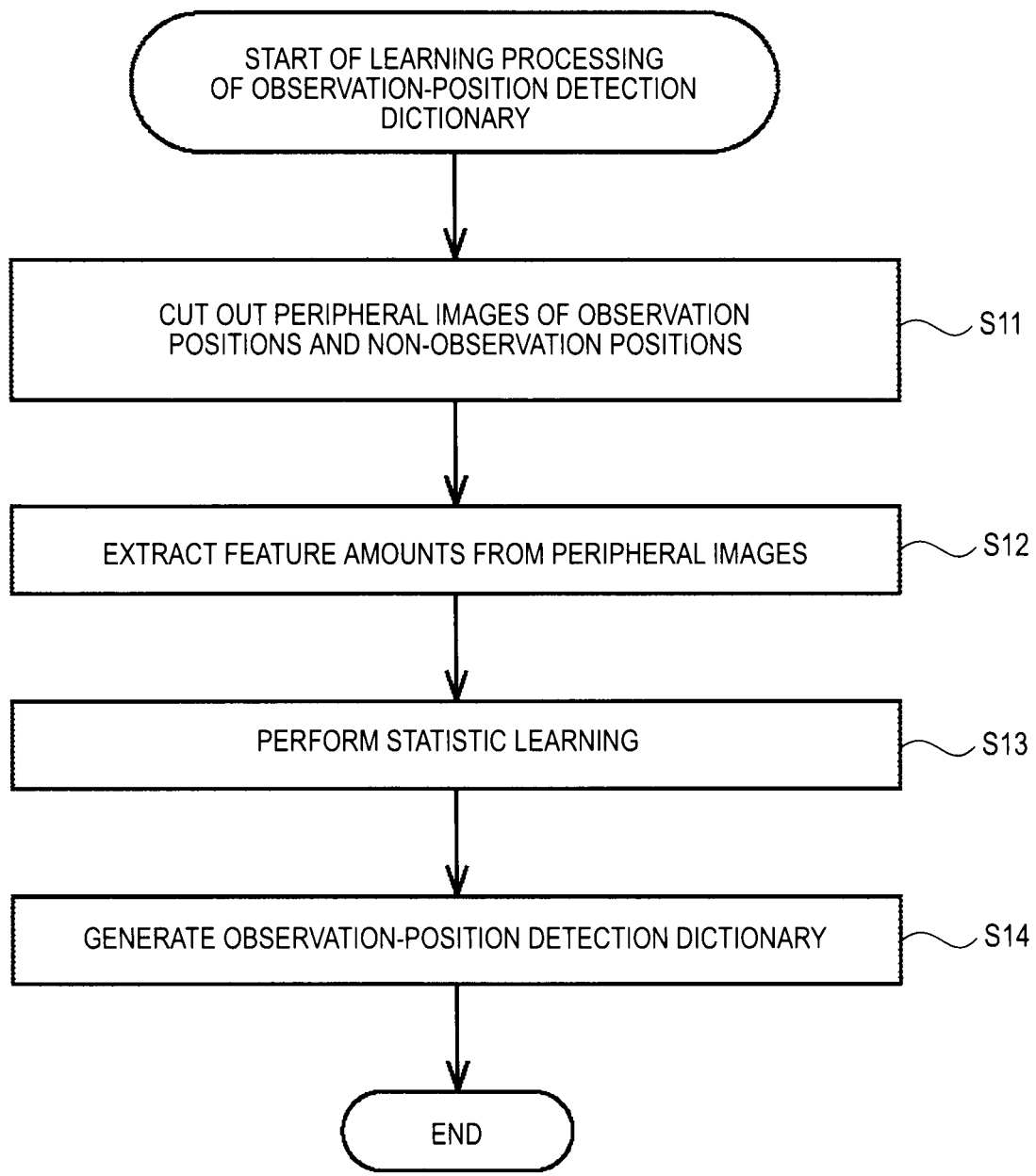
FIG. 8 is a flowchart for explaining learning processing of an observation-position detection dictionary.

Return to the explanation of the flowchart of FIG. 8, when the peripheral image generation unit 51 generates peripheral images from plural medical images for learning, the peripheral image generation unit 51 supplies these peripheral images to the feature-amount extraction unit 52, then, the process proceeds to Step S12.

In Step S12, the feature amount extraction unit 52 extracts feature amounts from respective peripheral images supplied from the peripheral image generation unit 51 and supplies the feature amounts to the learning unit 53 with the labels added to each peripheral image. For example, the feature amount extraction unit 52 pairs arbitrary two pixels on the peripheral image as a pixel pair and calculates the difference of luminance values of these pixels as the feature amount. The feature amount extraction unit 52 calculates the above-described feature amounts concerning some different pixel pairs on the peripheral image and supplies the amounts to the learning unit 53.

In Step S13, the learning unit 53 performs statistical learning such as Boosting based on the feature amounts supplied from the feature amount extraction unit 52, supplying the learning result to the dictionary generation unit 54.

For example, assume that a function $G(x)$ representing the degree of a feature of the observation position is a function obtained by linear combination, namely, by weighted addition of plural weak classifiers $g(x)$. Here, the weak classifier $g(x)$ is a function outputting "1" when the feature amount of a certain pixel pair is equal to or higher than a given threshold value "thg" and outputting "0" when the feature amount is lower than the threshold value "thg". Additionally, as a value obtained by substituting the feature amount extracted from the image into the function $G(x)$ is higher, the region of the image has a higher degree of the feature as the observation position.

In this case, the leaning unit 53 calculates the function $G(x)$ whereby the observation position can be detected most accurately by statistical learning while combining some weak classifiers $g(x)$ by using feature amounts obtained from positive data and feature amounts obtained by negative data. In other words, the optimum combination of the pixel pairs for detecting the observation position (combination of weak classifiers $g(x)$), the threshold value "thg" of each weak classifier $g(x)$ and weight used for linear combination are calculated in the statistical learning.

In Step S14, the dictionary generation unit 54 generates the observation-position detection dictionary based on the result of statistical learning supplied from the learning unit 53, supplying the dictionary to the observation-position detection dictionary holding unit 141 of the diagnostic moving image generation unit 25 to be held therein.

For example, the dictionary generation unit 54 generates the observation-position detection dictionary so as to include respective weak classifiers $g(x)$ included in the function $G(x)$, the threshold values "thg" of these weak classifiers and weights of respective weak classifiers used for the linear combination. When the observation-position detection dictionary is generated in this manner, the learning processing of the observation-position detection dictionary is completed.

The observation-position detection dictionary is generated in advance by statistical learning using the observation logs by the skillful doctor and the medical images for learning, thereby detecting the observation positions to which attention is assumed to be given by the skillful doctor or the like from an arbitrary medical image with high accuracy.

[Explanation of Learning Processing of Observation-Parameter Generation Dictionary]

Figure 10:
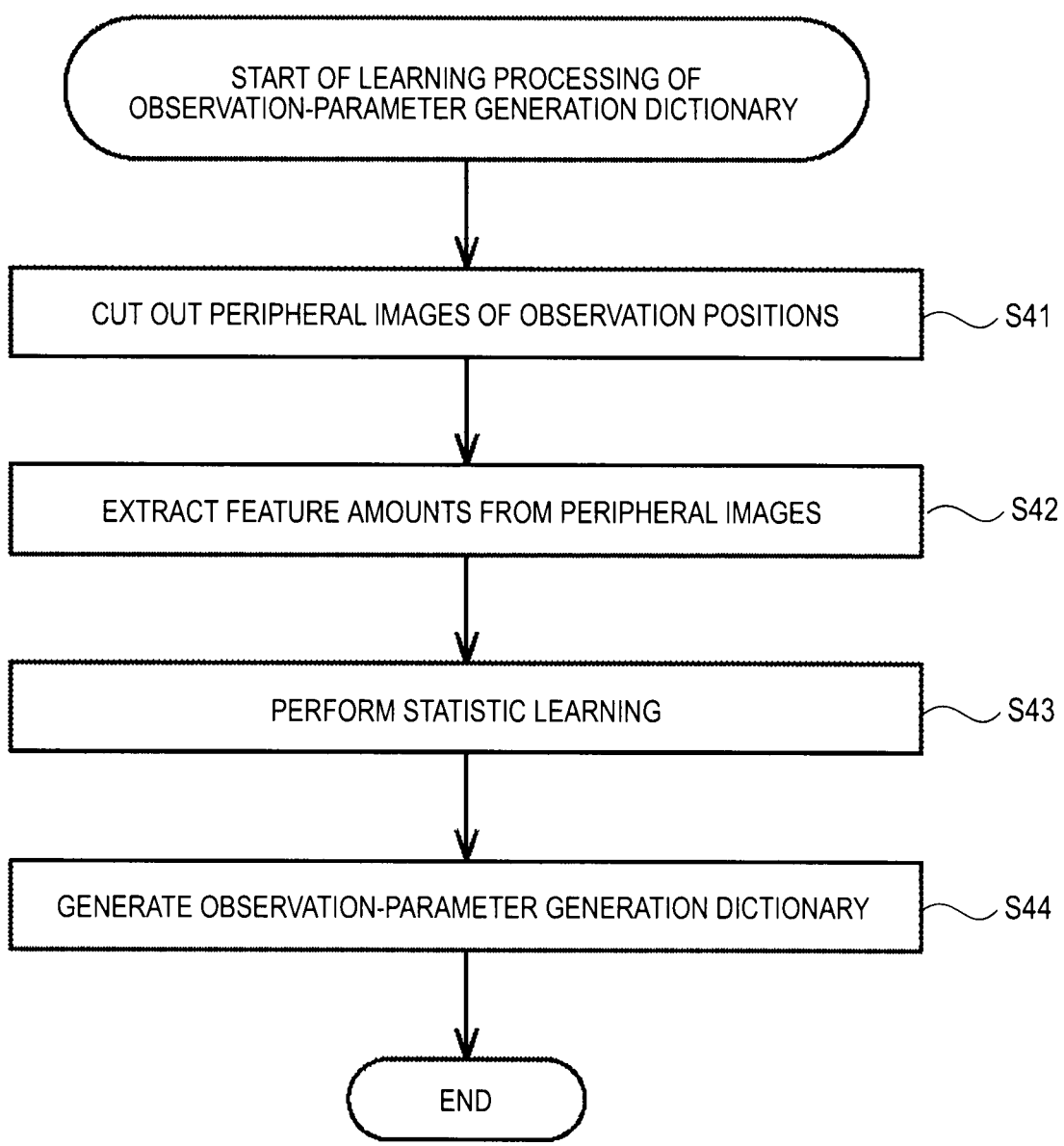
FIG. 10 is a flowchart for explaining leaning processing of an observation-parameter generation dictionary.

Next, learning processing of the observation-parameter generation dictionary by the observation-parameter generation dictionary generation unit 23 will be explained with reference to a flowchart of FIG. 10.

In Step S41, the peripheral image generation unit 81 cuts out peripheral images of observation positions on the medical image for learning based on the medical image for learning and the observation log supplied from the acquisition unit 21 and supplies the images to the feature amount extraction unit 82. That is, the same processing as the processing of cutting out peripheral images of observation positions performed in Step S11 of FIG. 8 is performed in Step S41.

In Step S42, the feature amount extraction unit 82 extracts feature amounts from respective peripheral images supplied from the peripheral image generation unit 81 and supplies the feature amounts to the learning unit 83. For example, a histogram representing distribution of luminance values of pixels in the peripheral images, HOG (Histogram of Oriented Gradients) and so on are calculated as the feature amounts.

In Step S43, the learning unit 83 performs statistical learning such as Gradient Boosting based on the feature amounts of respective peripheral images supplied from the feature amount extraction unit 82 and the observation logs supplied from the acquisition unit 21. That is, the statistical learning is performed by using respective observation parameters obtained from the observation logs as teacher data.

Figure 11:
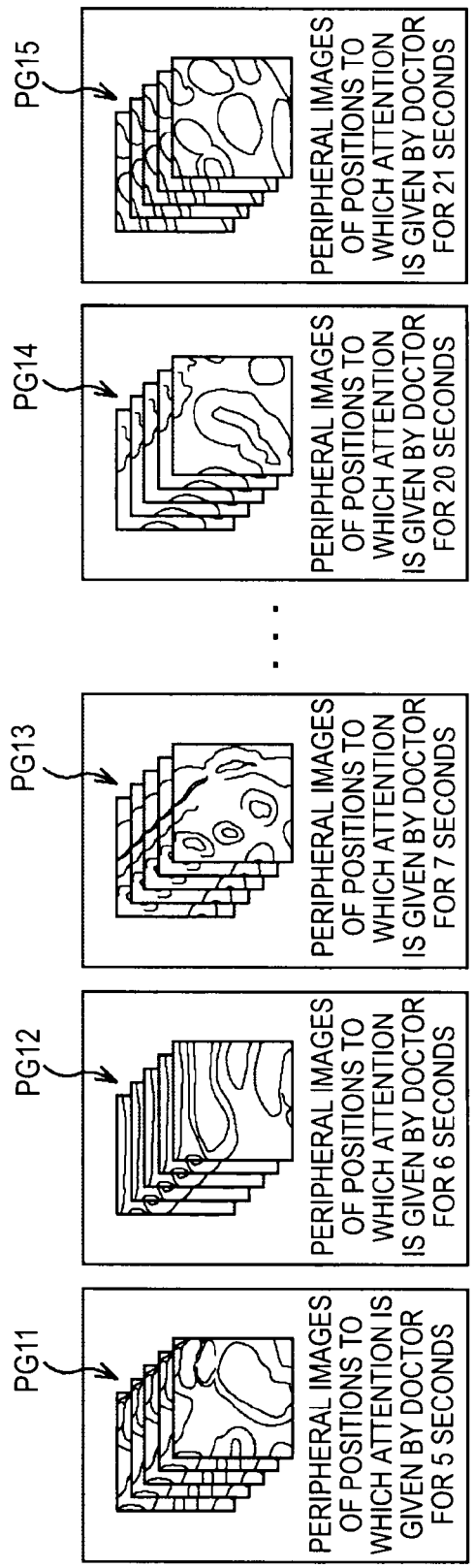
FIG. 11 is a view for explaining the learning of the observation-parameter generation dictionary.

For example, when the observation-parameter generation dictionary for obtaining observation time as observation parameter is generated, the learning unit 83 associates each peripheral image, more specifically, the feature amount extracted from the peripheral image with observation time of the observation position included in the peripheral image as shown in FIG. 11. For example, a peripheral image group PG11 to a peripheral image group PG15 including plural peripheral images are aggregates of peripheral images including observation positions observation time of which is 5 seconds, 6 seconds, 7 seconds, 20 seconds and 21 seconds respectively.

Then, the leaning unit 83 calculates the following expression (1) based on a feature amount "x" and an observation time "y" of each peripheral image to find a function F(x) with the minimum loss function L (y, F(x)).

$$F' = \operatorname*{argmin}_{F} E_{x,y}(L(y, F(x))) \quad (1)$$

Here, the function F(x) is a function for obtaining the observation parameter (observation time "y" in this case) from the feature amount "x" extracted from an arbitrary image including the observation position. In the expression (1), Ex, y(L(y, F(x)) are expected values of the loss function L (y, F(x)). The statistical learning is formulated as a case of estimating the function F' with the minimum loss function.

After the statistical learning is performed with respect to each observation parameter, the leaning unit 83 supplies the learning result to the dictionary generation unit 84.

In Step S44, the dictionary generation unit 84 generates the observation-parameter generation dictionary of each observation parameter based on the learning result supplied from the learning unit 83, supplying the dictionary to the observation-parameter generation dictionary holding unit 142 to be held therein.

For example, the dictionary generation unit 84 generates the observation-parameter generation dictionary in which observation time is the observation parameter of the function F(x). When the observation-parameter generation dictionary is generated in this manner, the learning processing of the observation-parameter generation dictionary is completed.

The observation-parameter generation dictionary is generated in advance by statistical learning by using the observation logs by the skillful doctor and the medical images for learning, thereby estimating which parameter is used for observing respective observation positions of an arbitrary medical image by the skillful doctor or the like with high accuracy.

[Explanation of Learning Processing of Observation-Order Generation Dictionary]

Figure 12:
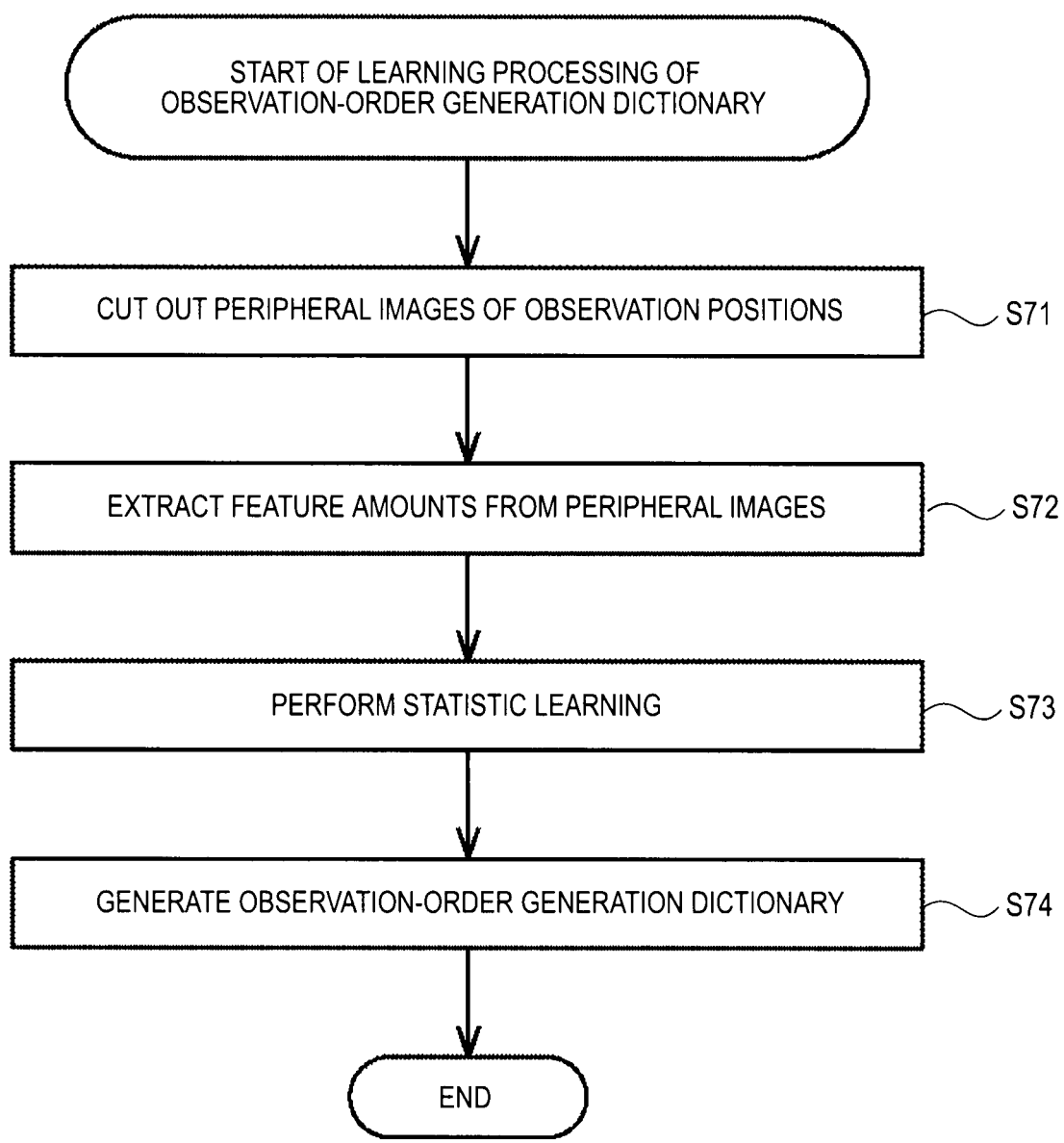
FIG. 12 is a flowchart for explaining learning processing of an observation-order generation dictionary.

Moreover, learning processing of the observation-order generation dictionary by the observation-order generation dictionary generation unit 24 will be explained with reference to a flowchart of FIG. 12.

In Step S71, the peripheral image generation unit 111 cuts out peripheral images of observation positions on the medical image for learning based on the medical image for learning and the observation log supplied from the acquisition unit 21 and supplies the images to the feature amount extraction unit 112. That is, the same processing as the processing of cutting out peripheral images of observation positions performed in Step S71 of FIG. 8 is performed in Step S11.

In Step S72, the feature amount extraction unit 112 extracts feature amounts from respective peripheral images supplied from the peripheral image generation unit 111 and supplies the feature amounts to the learning unit 113. For example, the histogram representing distribution of luminance values of pixels in the peripheral image, the HOG and so on are calculated as the feature amounts.

In Step S73, the learning unit 113 performs statistical learning such as Rank Boost based on the feature amounts of respective peripheral images supplied from the feature amount extraction unit 112 and the observation logs supplied from the acquisition unit 21. That is, the statistical learning is performed by using the observation order of observation positions obtained from the observation logs as teacher data.

Figure 13:
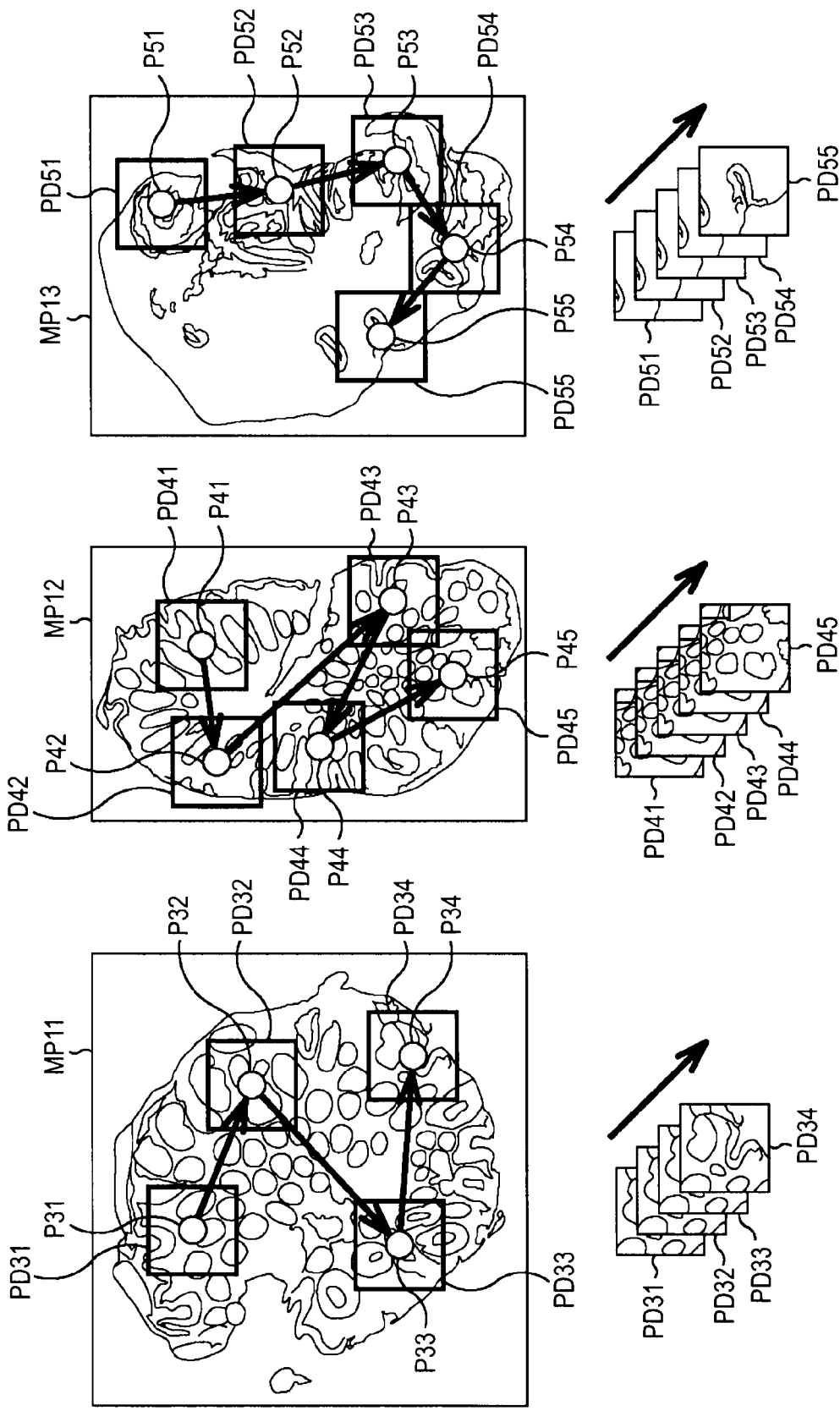
FIG. 13 is view for explaining the learning of the observation-order generation dictionary.

For example, as shown in FIG. 13, peripheral images are cut out from medical images for learning MP11 to MP13 as shown in FIG. 13.

In the example of FIG. 13, peripheral images PD 31 to PD 34 including observation positions P31 to P34 at centers of the images are cut out from the medical image for learning MP11. The peripheral images PD41 to PD45 including observation positions P41 to P45 at centers of the images are cut out from the medical image for learning MP12, and the peripheral images PD51 to PD55 including observation positions PD51 to PD55 are cut out from the medical image for learning MP13.

In the above case, the learning unit 113 sorts peripheral images cut out from these medical images for learning in the observed order based on the observation log in each medical image for learning. As information concerning respective observation positions is sorted in time series in the observation log, the observation order (display order) of peripheral images including these observation positions can be determined by referring to the observation log.

For example, when observation has been made by the skillful doctor in the order from the observation position P31 to the observation position P34 on the medical image for learning MP11, the learning unit 113 sorts the peripheral images cut out from the medical image for learning MP11 in the order from the peripheral image PD31 to the peripheral image PD34.

In the same manner, the learning unit 113 sorts peripheral images cut out from the medical image for learning MP12 in the order from the peripheral image PD41 to the peripheral image PD45 by referring to the observation log. The learning unit 113 also sorts the peripheral images cut out from the medical image for learning MP13 in the order from the peripheral image PD51 to the peripheral image PD55.

More specifically, the learning unit 113 sorts feature amounts of the peripheral images cut out from the medical image for learning in ascending order or descending order in each medical image for learning.

After sorting the feature amounts, the learning unit 113 calculates a score function H(x) with the minimum loss function $rloss_D(H)$ represented by the following expression (2) based on the feature amount "x" of each peripheral image.

$$rloss_D(H) = \sum_{x_0, x_1} D(x_0, x_1)[[H(x_1) \leq H(x_0)]] \quad (2)$$

In the expression (2), $[[H(x_1) \leq H(x_0)]]$ is an operator outputting "1" when $H(x_1) \leq H(x_0)$ is satisfied and outputting "0" when $H(x_1) \leq H(x_0)$ is not satisfied. Additionally, $D(x_0, x_1)$ in the expression (2) represents weight.

The score function H(x) is a function obtained by performing linear combination of weak classifiers ht(x) by using a weight $\alpha_t$ as shown in the following expression (3), and a value of the score function H(x) indicates the degree in which attention should be given at the time of performing pathological diagnosis.

$$H(x) = \Sigma_t^T \alpha_t h_t(x) \quad (3)$$

The weak classifier ht(x) in the expression (3) is a function outputting "1" when the feature amount "x" of the peripheral image is equal to or higher than a given threshold value "tho", and outputting "0" when the feature amount "x" is lower than the threshold value "tho". More specifically, the feature amount "x" to be substituted into the weak classifier ht(x) is, for example, a frequency value of one of bins forming a histogram of luminance values extracted from the peripheral image as the feature amount, and weak classifiers are set with respect to given T-bins of bins forming the histogram.

The learning unit 113 calculates the score function H(x) in each peripheral image extracted from one medical image for learning and substitutes each score function H(x) into the above expression (2) to thereby calculate the loss function $rloss_D(H)$.

That is, assume that, when arbitrary two peripheral images make a pair from the peripheral images extracted from one medical image for learning, K-types of pairs are made in total, the learning unit 113 performs an operation of an operator [[ ]] with respect to respective K-pairs. For example, when a peripheral image $PDx_0$ and a peripheral image $PDx_1$ are a pair, and the observation order of the peripheral image $PDx_0$ is earlier, the operation of $[[H(x_1) \leq H(x_0)]]$ is performed based on a score function $H(x_0)$ of the peripheral image $PDx_0$ and a score function $H(x_1)$ of the peripheral image $PDx_1$.

The learning unit 113 performs operation of the operator [[ ]] with respect to all possible pairs of peripheral images, then, linear combination is performed by multiplying these operation result by a weight $D(x_0, x_1)$ to thereby calculate a value of the loss function $rloss_D(H)$. As described above, the learning unit 113 calculates values of the loss function while changing the combination of weak classifiers ht(x) forming the score function H(x), the weight $\alpha_t$ and the threshold value "tho" of the weak classifiers to thereby calculate the score function H(x) with the minimum loss function.

The Rank Boost performed as described above is a method of learning the score function H(x) ranking candidates by Boosting. When the statistical learning is performed, the learning unit 113 supplies the learning result to the dictionary generation unit 114 and the process proceeds to Step S74.

In Step S74, the dictionary generation unit 114 generates the observation-order generation dictionary based on the learning result supplied from the learning unit 113, supplying the dictionary to the observation-order generation dictionary holding unit 143 of the diagnostic moving image generation unit 25 to be held therein.

For example, the dictionary generation unit 114 generates the observation-order generation dictionary so as to include the combination of weak classifiers ht(x) forming the score function H(x), the threshold value "tho" of respective weak classifiers and the weight $\alpha_t$. When the observation-order generation dictionary is generated in this manner, the learning processing of the observation-order generation dictionary is completed.

The observation-order generation dictionary is generated in advance by statistical learning by using the observation logs by the skillful doctor and the medical images for learning, thereby estimating in what order the skillful doctor or the like observes respective observation positions of an arbitrary medical image with high accuracy.

At the time of the learning of the observation-order generation dictionary, respective peripheral images extracted from the medical image for learning are sorted in the observed order, which is in descending order of degree of attention by the skillful doctor or the like who has made a pathological diagnosis by using the medical image for learning.

For example, the descending order of degree of attention is the descending order of tumor progress of cancer as regions of observation positions, which is determined to some degree according to lesions as targets for pathological diagnosis.

However, the criteria of judgment for the degree of attention with respect to respective regions may differ according to doctors at the time of pathological diagnosis. For example, some doctors observe respective tumors in descending order of progress of tumors and some doctors observe tumors in the order from a region where the tumor is malignant or not is ambiguous when making diagnosis of cancer.

In response to the above, each doctor generates the observation-order generation dictionary by allowing the learning processing to be performed by exclusively using medical images for learning which have been used for pathological diagnoses by the doctor himself/herself, thereby ordering observation positions in the order of degree of attention more accurately.

For example, when a certain doctor makes a pathological diagnosis by using a new medical image, it is possible to estimate the observation order of respective observation positions more accurately by using the observation-order generation dictionary obtained by the medical images for learning used for pathological diagnoses by the doctor. That is, in the medical image to be a new target of diagnosis this time, respective observation positions detected from the medical image can be sorted in the anticipated order of observation to be made by the doctor.

[Explanation of Moving Image Generation Processing]

Figure 14:
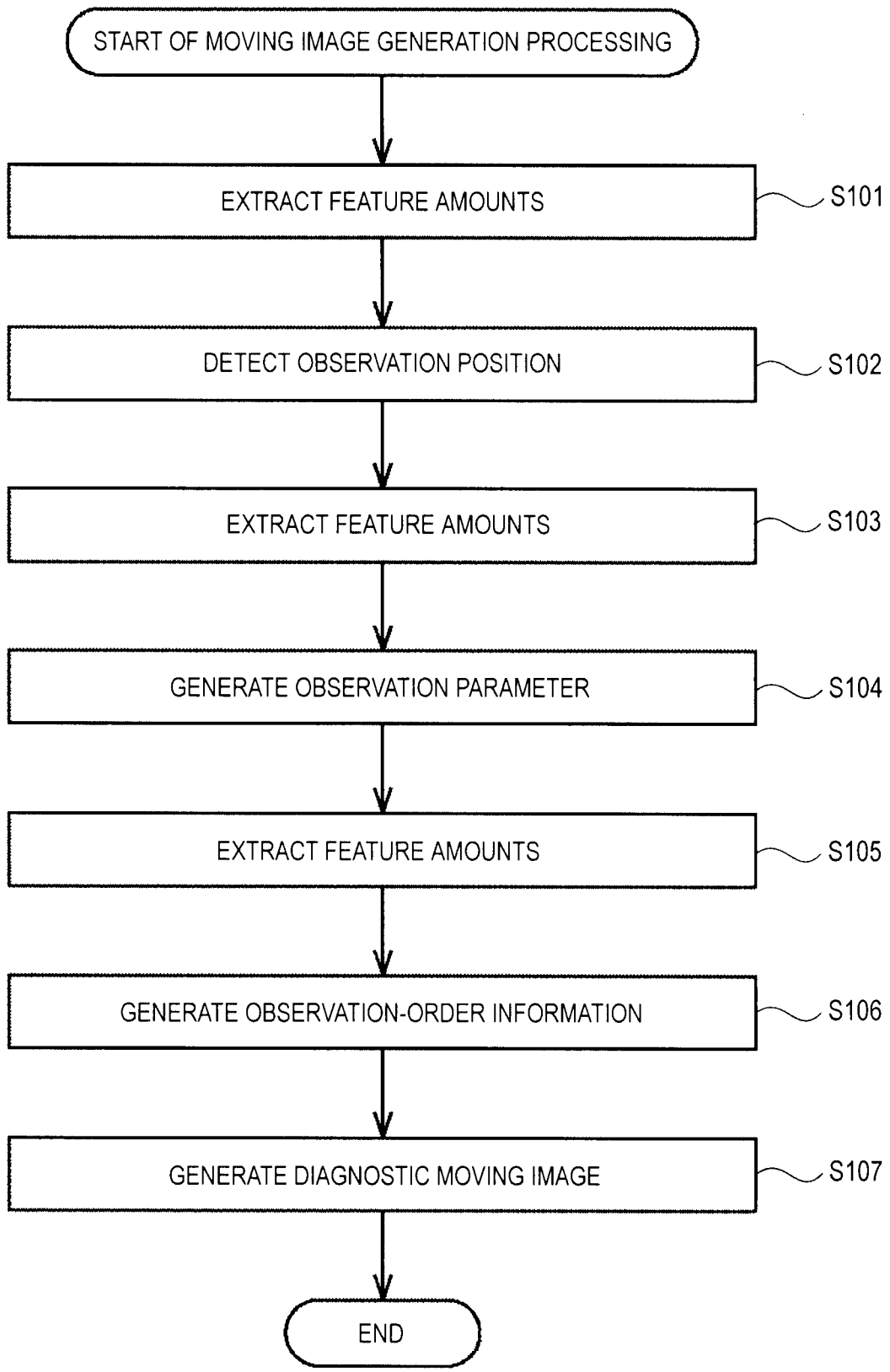
FIG. 14 is a flowchart for explaining moving image generation processing.

When respective dictionaries are generated as described above, a diagnostic moving image can be generated. The diagnostic moving image generation unit 25 of the image processing unit 11 starts moving image generation processing to generate a diagnostic moving image when a medical image is inputted and generation of the diagnostic moving image is instructed by the doctor or the like. Hereinafter, moving image generation processing by the diagnostic moving image generation unit 25 will be explained with reference to a flowchart of FIG. 14.

In Step S101, the feature amount extraction unit 161 of the observation-position detection unit 144 extracts feature amounts from the supplied medical image. For example, the feature amount extraction unit 161 takes a region with a given size on the medical image as an image for detection and extracts the difference of luminance values of particular pixel pairs on the image for detection as the feature amount in each image for detection by changing the position of the image for detection.

In Step S102, the observation-position detection unit 144 detects observation positions from the medical image based on the feature amounts extracted by the feature amount extraction unit 161 and the observation position detection dictionary held in the observation-position detection dictionary holding unit 141.

For example, the observation-position detection unit 144 determines the central position of the image for detection as the observation position when the feature amount "x" extracted from each image for detection is substituted into the function G(x) obtained from the observation-position detection dictionary and the obtained value of the function G(x) is higher than "0" in each image for detection.

When detecting the observation position from the medical image, the observation-position detection unit 144 supplies information indicating the detected observation positions and the medical image to the observation-parameter generation unit 145, the observation-order information generation unit 146 and the moving image generation unit 147. The observation-position detection unit 144 also supplies values of the function G(x) representing the degree of a feature of the observation position calculated with respect to respective observation positions to the moving image generation unit 147.

In Step S103, the feature amount extraction unit 162 of the observation-parameter generation unit 145 extracts feature amounts from the medical image based on information indicating the observation positions and the medical image supplied from the observation position detection unit 144. For example, the feature amount extraction unit 162 extracts, for example, the histogram representing distribution of luminance values of pixels in the given region including the observation position as the feature amount with respect to each observation position on the medical image.

In Step S104, the observation-parameter generation unit 145 generates an observation parameter based on the feature amounts extracted by the feature amount extraction unit 162 and the observation-parameter generation dictionary held in the observation-parameter generation dictionary holding unit 142.

For example, the observation-parameter generation unit 145 substitutes the feature amount "x" of each observation position into the function F(x) acquired as the observation-parameter dictionary to take the value to be fixed by the obtained value of the function F(x) as the observation parameter.

That is, the range of values which can be taken as output values of the function F(x) is divided into some ranges in advance and values of the observation parameters are associated with these divided ranges. The observation-parameter generation unit 145 determines to which range in previously-divided ranges the output value of the function F(x) obtained by substituting the feature amount belongs, thereby setting the value associated with the determined range as the value of the observation parameter.

The observation-parameter generation unit 145 supplies respective observation parameters obtained as described the above to the moving image generation unit 147.

In Step S105, the feature amount extraction unit 163 of the observation-order information generation unit 146 extracts feature amounts based on information indicating observation positions and the medical image supplied from the observation-position detection unit 144. For example, the feature amount extraction unit 163 extracts, for example, the histogram representing distribution of luminance values of pixels in the given region including the observation position as the feature amount with respect to each observation position on the medical image.

In Step S106, the observation-order information generation unit 146 generates observation order information based on the feature amounts extracted by the feature amount extraction unit 163 and the observation-order generation dictionary held in the observation-order generation dictionary holding unit 143.

For example, the observation-order information generation unit 146 substitutes the feature amount "x" of each observation position into the score function H(x) obtained from the observation-order generation dictionary to calculate a value of the score function H(x). Then, the observation-order information generation unit 146 sorts respective observation positions in descending order of values of the score function H(x) and sets the order as the observation order of observation positions.

The observation-order information generation unit 146 supplies observation order information indicating the observation order obtained as described above to the moving image generation unit 147.

In Step S107, the moving image generation unit 147 generates a diagnostic moving image based on information indicating observation positions, the medical image and values of the function G(x) supplied from the observation-position detection unit 144, observation parameters supplied from the observation-parameter generation unit 145 and observation order information supplied from the observation-order information generation unit 146.

For example, assuming a case where the same image as the medical image for learning MP11 shown in FIG. 13 is inputted as the medical image (hereinafter, referred to also as a medical image MP11) and the order of respective observation positions to be observed shown by the observation order information is from the observation position P31 to the observation position P34.

In such case, for example, the moving image generation unit 147 generates a moving image in which the whole medical image MP11 is displayed first, then, regions including the observation positions P31 to P34 are sequentially displayed and finally the whole medical image MP11 is displayed again as the diagnostic moving image.

That is, when the diagnostic moving image is reproduced, the whole medical image MP11 is displayed after starting reproduction, then, a region including the first observation position P31 is displayed with observation parameters of the observation position P31. For example, the region including the observation position P31 at the center of the region on the medical image MP11 is displayed with the display magnification (zooming magnification) as the observation parameter continuously for the observation time as the observation parameter.

Next, the region between the observation position P31 and the observation position P32 is scrolled and the region including the observation position P32 at the center of the region is displayed with observation parameters of the observation position P32. That is, regions including respective positions on the medical image MP11 are displayed while the position on the medical image MP11 to be displayed at the center of the diagnostic moving image is moved from the observation position P31 to the observation position P32.

At this time, the display magnification as the observation parameter may differ between the observation position P31 and the observation position P32. In such case, the display magnification can be changed after the scrolling display from the observation position P31 to the observation position P32 is completed, or the display magnification can be changed continuously during the scrolling display. That is, the region including the observation position P32 is displayed with the observation parameter of the observation position P32 when the observation position P32 is displayed at the center of the diagnostic moving image.

After the region including the observation position P32 is displayed, the region including the observation position P33 and the region including the observation position P34 are sequentially displayed with observation parameters of these observation positions while scrolling display between observation positions is performed appropriately in the same manner as the above. When the whole medical image MP11 is displayed again after the region including the observation position P34 is displayed, the reproduction of the diagnostic moving image is completed.

As described above, the display magnification, the observation order and the like change in accordance with the degree of attention in respective observation positions, the size of portions to be observed and so on in the diagnostic moving image. For example, a serious tumor as the observation position is zoomed in with a high magnification rate and scrolled slowly. In the case where the tumor region is large, the region is displayed with a low magnification rate so that the whole tumor is displayed.

Particularly, concerning the observation position in which the function $G(x)$ indicating the degree of a feature of the observation position is higher than the predetermined threshold value in observation positions displayed in the diagnostic moving image, the diagnostic moving image is generated so that the observation position is displayed in a display format and the like different from the display of other observation positions. Specifically, when the region of the observation position the function $G(x)$ of which is higher than the threshold value is displayed, for example, a frame surrounding the diagnostic moving image is displayed or the diagnostic moving image is displayed with blinking. It is also preferable that an alarm sound is activated with the display in a particular display format at the time of displaying the region of such observation position.

The value of the function $G(x)$ represents the degree of a feature of the observation position, namely, the degree in which attention should be given. For example, a portion of a progressed tumor will be a portion having a high degree of attention. Accordingly, the moving image generation unit 147 displays the observation position in which the value of the function $G(x)$ is higher than the given threshold value in the display format different from other observation positions in the diagnostic moving image as the observation position where the portion to which a higher degree of attention should be given is displayed. Consequently, the attention of the doctor or the like observing the diagnostic moving image is directed to the position.

When an operation is performed with respect to the image processing device 11 by the doctor or the like in a state in which a region including one observation position is displayed as the diagnostic moving image at the time of reproducing the diagnostic moving image, the region including the next observation position or the region including the previous observation position can be displayed in accordance with the operation. That is, the previous or next observation position can be displayed according to the instruction by the doctor or the like.

When the diagnostic moving image is generated, the moving image generation unit 147 supplies the generated diagnostic moving image to the recording unit 26 to be recorded therein, and the moving image generation processing is completed. The diagnostic moving image recorded in the recording unit 26 is read out and reproduced appropriately by the display control unit 27.

As described above, the diagnostic moving image generation unit 25 determines the positions to be observed, observation parameters, the observation order and the like from the medical image to be processed by using respective dictionaries generated in advance by learning and generates a diagnostic moving image from the medical image based on the observation positions and the like.

Accordingly, pathological images for diagnosis can be obtained more simply and swiftly. That is, when using respective dictionaries held in the diagnostic moving image generation unit 25, the screen operation which is assumed to be performed by the skillful doctor or the like when making a diagnosis by using an arbitrary medical image inputted anew can be simulated without complicated input operation by the physician or the like.

As the result of the simulation, the diagnostic moving image can be obtained, in which respective observation positions which are assumed to be noticed by the skillful doctor or the like are displayed in the order of observation assumed to be made by the skillful doctor or the like. That is, operations of the screen at the time of giving a diagnosis by the skillful doctor such as zooming-in/zooming-out, scrolling and so on of a particular portion are automatically performed only by inputting the target medical image and instructing the generation of a diagnostic moving image for the doctor or the like who intends to make a pathological diagnosis using the medical image.

Therefore, when the diagnostic moving image generated in the manner described above is reproduced, portions necessary for diagnosis of a tumor or the like are displayed more efficiently and effectively, therefore, the doctor or the like can make a diagnosis more efficiently and can shorten time for diagnosis. Additionally, not only portions of respective observation positions but also the whole medical image is displayed in the diagnostic moving image, therefore, it is possible to prevent oversight of the position which should be observed by the doctor even when there is omission in extraction of observation positions by image recognition using dictionaries.

The diagnostic moving image obtained in the above manner can be used not only for actual pathological diagnosis but also other applications such as a teaching material for leaning. For example, when dictionaries are generated by learning using an observation log by an advising doctor, the diagnostic moving image generated by using the dictionaries can be used as the teaching material for learning for a doctor with low skill level.

In the above example, display magnification and observation time are explained as examples of observation parameters, and display direction (angle) of the observation position, scrolling speed at a portion between observation positions and so on can be used as observation parameters. Additionally, the display order, the display magnification and so on of respective observation positions can be set by the doctor or the like.

MODIFICATION EXAMPLE 1

The diagnostic moving image can apply any form as long as respective observation positions are displayed in the observation order determined by dictionaries.

For example, when respective observation positions are displayed with the observation parameters determined by dictionaries, it is preferable that, after the display of one observation position is completed, the whole medical image is displayed once, then, the next observation position is displayed.

Specifically, for example, assume that the above medical image MP11 is inputted as the medical image and the order in which respective observation positions should be observed indicated by observation order information is from the observation position P31 to the observation position P34.

In such case, for example, the moving image generation unit 147 generates a diagnostic moving image in which the whole medical image MP11 is displayed between the display of the observation position and the display of the next observation position.

That is, at the time of reproducing the diagnostic moving image, the whole medical image MP11 is displayed first, then, the region including the observation position P31 is displayed. After that, display is performed in the order of the region including the observation position P32, the whole medical image MP11, the region including the observation position P33, the whole medical image MP11, the region including the observation position P34 and the whole medical image MP11.

MODIFICATION EXAMPLE 2

It is also preferable that the region in which the whole medical image is constantly displayed is provided on the diagnostic moving image as shown in the region RA11 of FIG. 6.

Specifically, for example, assume that the above medical image MP11 is inputted as the medical image and the order in which respective observation positions should be observed indicated by observation order information is from the observation position P31 to the observation position P34.

In such case, for example, the moving image generation unit 147 generates a diagnostic moving image in which regions including observation positions P31 to P34 are sequentially displayed on the whole screen with observation parameters of these observation positions in a state in which the whole medical image MP11 is displayed in a partial region of the screen.

The diagnostic moving image explained in the manner described above is the moving image in which the image of the region including the observation position forms one frame, and it is also preferable that still images of regions including respective observation positions generate a group of still images which are aligned (ordered) in the observation order. For example, the group of still images can be the image group obtained by aligning images of respective frames included in the diagnostic moving image in the order of frames. The screen operation by the skillful doctor at the time of diagnosis can be simulated by using such group of still images.

It is also preferable that the doctor or the like can set the time limit or reproduction time such as three minute or one minute at the time of generating the diagnostic moving image. In such case, for example, the moving image generation unit 147 generates an moving image having the set reproduction time as the diagnostic moving image.

Specifically, the moving image generation unit 147 changes observation time of respective observation positions obtained as the observation parameter while maintaining the ratio of the observation time so that the sum of display time of respective observation positions in the diagnostic moving image will be the set reproduction time. Accordingly, the diagnostic moving image which is reproduced within the designated period of time can be obtained while maintaining the ratio in the length of time during which respective observation positions are displayed.

It is also preferable that some observation positions with lower values of the function $G(x)$ are thinned out so that the reproduction time of the diagnostic moving image will be within the designated period of time. That is, the diagnostic moving image in which a given number of observation positions are selected in ascending order of the degree of attention and the selected observation positions are not displayed (are excluded) is generated in this case.

The series of processing described above can be executed by hardware as well as by software. When the series of processing is executed by software, a computer in which programs included in the software are incorporated in dedicated hardware is used, or the software is installed from program recording media, for example, on a general-purpose computer capable of executing various functions by installing various programs.

Figure 15:
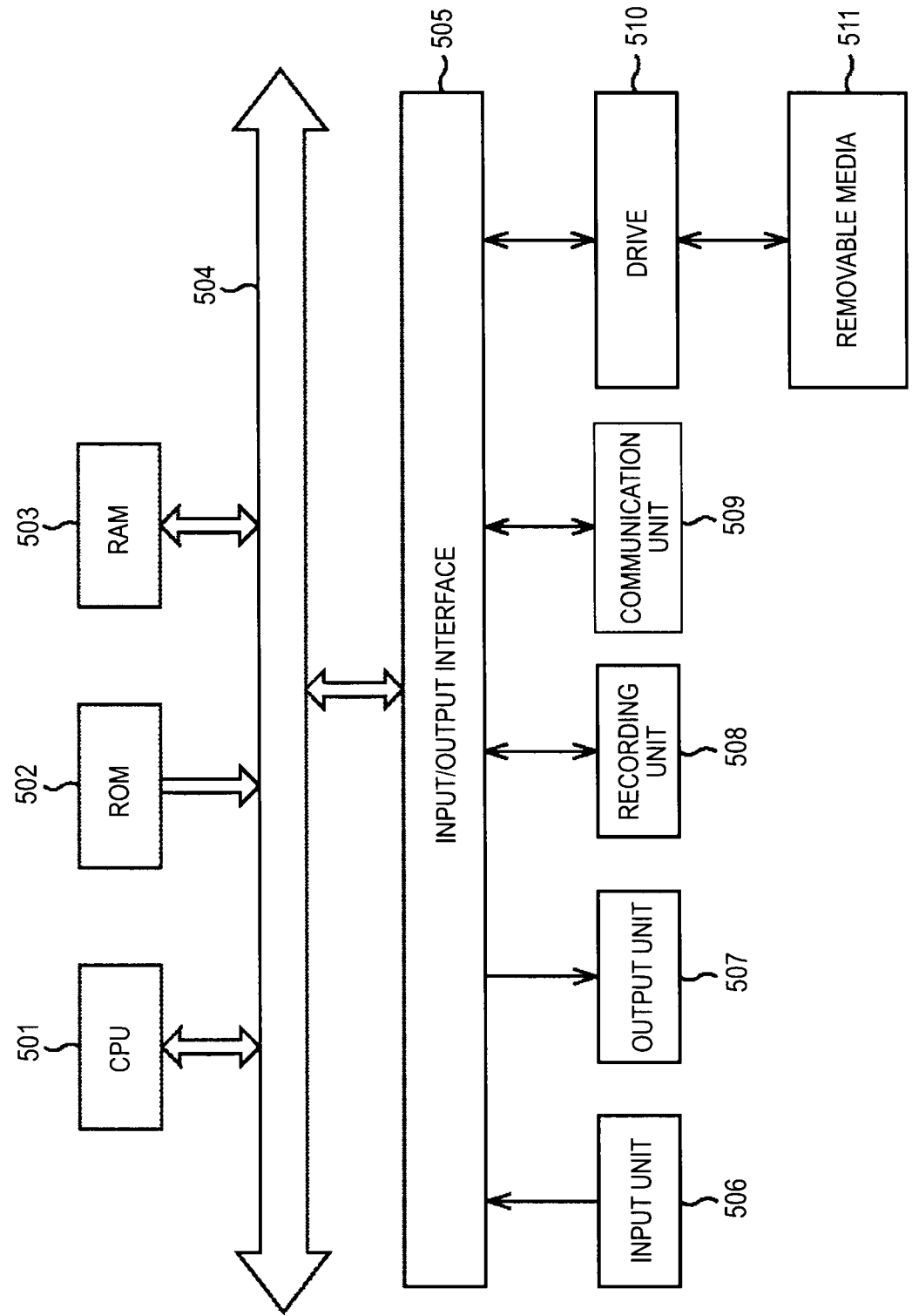
FIG. 15 is a diagram showing a configuration example of a computer.

FIG. 15 is a block diagram showing a configuration example of hardware of a computer executing the above series of processing by programs.

In the computer, a CPU 501, a ROM (Read Only Memory) 502 and a RAM (Random Access Memory) 503 are connected to one another by a bus 504.

An input/output interface 505 is further connected to the bus 504. To the input/output interface 505, an input unit 506 including a keyboard, a mouse, a microphone and the like, an output unit 507 including a display, a speaker and the like, a recording unit 508 including a hard disc, a non-volatile memory and the like, a communication unit 509 including a network interface and a drive 510 driving removable media 511 such as a magnetic disc, an optical disc, a magneto-optical disc and a semiconductor memory are connected.

In the computer having the above configuration, for example, when the CPU 501 loads programs recorded in the recording unit 508 to the RAM 503 through the input/output interface 505 and the bus 504 and executes the programs, the above series of processing is performed.

The programs executed by the computer (CPU 501) are provided by being recorded in removable media 511 which are packaged media such as a magnetic disc (including a flexible disc), an optical disc (CD-ROM (Compact Disc-Read Only Memory), a DVD (Digital Versatile Disc) and so on), a magneto-optical disc and a semiconductor memory, or provided through wired or wireless transmission media such as a local area network, Internet and a digital satellite broadcasting.

The programs can be installed on the recording unit 508 through the input/output interface 505 by mounting the removable media 511 on the drive 510. The programs can be also installed on the recording unit 508 by being received by the communication unit 509 through wired or wireless transmission media. Additionally, programs can be installed in the ROM 502 or the recording unit 508 in advance.

The programs executed by the computer can be programs processed in time series along the order explained in the present specification as well as programs processed in parallel or at necessary timing, for example, when calling is performed.

The present disclosure is not limited to the above-described embodiment and can be variously modified within a scope not departing from the gist of the present disclosure.

The present disclosure contains subject matter related to that disclosed in Japanese Priority Patent Application JP 2011-012952 filed in the Japan Patent Office on Jan. 25, 2011, the entire content of which is hereby incorporated by reference.

What is claimed is:

1. An image processing device comprising:
   circuitry configured to:
   extract first feature amounts from an image to be processed;
   detect observation positions from the image to which attention should be paid by applying a position detection dictionary to the first feature amounts extracted from the image, wherein the position detection dictionary is generated by statistical learning in advance;
   extract a second feature amount from each of the detected observation positions on the image, wherein the second feature amount is a distribution of pixel luminance values in a respective observation position;
   determine an order of observing the observation positions on the image by applying an order generation dictionary to the distribution of pixel luminance values of the observation positions on the image, wherein the order generation dictionary is generated based on an observation log obtained by observing regions of images in the past for statistical learning; and
   generate observation images for displaying the observation positions on the image in the determined order.

2. The image processing device according to claim 1, wherein the image is a medical image.

3. The image processing device according to claim 2, wherein the circuitry is further configured to:
   extract a third feature amount from each of the detected observation positions on the image; and
   determine an observation condition in each of the detected observation positions on the image by applying an observation-condition generation dictionary to the third feature amount, wherein the observation-condition generation dictionary is generated by statistical learning in advance, and
   wherein the circuitry generates the observation images such that each of the detected observation positions is displayed with the corresponding determined observation condition.

4. The image processing device according to claim 3, wherein the observation conditions are display magnifications of respective observation positions or display time during which the respective observation positions are continuously displayed.

5. The image processing device according to claim 2, wherein the observation images are moving images in which the detected observation positions are sequentially displayed in the determined order, and the medical image is displayed at least at the first or at the last of the moving images.

6. The image processing device according to claim 2, wherein the observation images are moving images in which the observation positions are sequentially displayed in the determined order, with the medical image being displayed between successive display of the detected observation positions.

7. The image processing device according to claim 2, wherein the observation images are moving images in which the observation positions are sequentially displayed in the determined order in a state in which the medical image is continuously displayed in a partial region in the observation images.

8. An image processing method comprising:
   in an image processing device:
   extracting first feature amounts from an image to be processed;
   detect observation positions from the image to which attention should be paid by applying a position detection dictionary to the first feature amounts extracted from the image, wherein the position detection dictionary is generated by statistical learning in advance;
   extracting a second feature amount from each of the detected observation positions on the image, wherein the second feature amount is a distribution of pixel luminance values in a respective observation position;
   determining an order of observing the observation positions on the image by applying an order generation dictionary to the distribution of pixel luminance values of the observation positions on the image, wherein the order generation dictionary is generated based on an observation log obtained by observing regions of for statistical learning; and
   generating observation images for displaying the observation positions on the image in the determined order.

9. A non-transitory computer-readable medium having stored thereon, a set of computer-executable instructions for causing the computer to perform steps comprising:
   extracting first feature amounts from an image to be processed;
   detecting observation positions from the image to which attention should be paid by applying a position detection dictionary to the first feature amounts extracted from the image, wherein the position detection dictionary is generated by statistical learning in advance;
   extracting a second feature amount from each of the detected observation positions on the image, wherein the second feature amount is a distribution of pixel luminance values in a respective observation position;
   determining an order of observing the observation positions on the image by applying an order generation dictionary to the distribution of pixel luminance values of the observation positions on the image, wherein the order generation dictionary is generated based on an observation log obtained by observing regions of images in the past for statistical learning; and
   generating observation images for displaying the observation positions on the image in the determined order.

* * * * *